(12) United States Patent
Wilkinson

(10) Patent No.: US 6,832,992 B2
(45) Date of Patent: Dec. 21, 2004

(54) PASSIVE SAFETY DEVICE FOR NEEDLE OF BLOOD COLLECTION SET

(75) Inventor: Bradley M. Wilkinson, North Haledon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 10/724,804

(22) Filed: Dec. 1, 2003

(65) Prior Publication Data

US 2004/0111057 A1 Jun. 10, 2004

Related U.S. Application Data

(63) Continuation-in-part of application No. 10/370,924, filed on Feb. 20, 2003, which is a continuation-in-part of application No. 09/521,078, filed on Mar. 7, 2000, now Pat. No. 6,537,259.

(51) Int. Cl.[7] .................. A61M 5/00; A61M 5/32; A61B 5/00
(52) U.S. Cl. ................ 604/110; 604/198; 600/576
(58) Field of Search ................ 604/263, 171, 604/192, 198, 110, 164.08, 165.01, 165.03, 240; 128/919; 600/576, 573

(56) References Cited

U.S. PATENT DOCUMENTS

| | | |
|---|---|---|
| 4,790,828 A | 12/1988 | Dombrowski et al. |
| 4,867,172 A | 9/1989 | Haber et al. |
| 4,955,866 A | 9/1990 | Corey |
| 5,059,180 A | 10/1991 | McLees |
| 5,176,655 A | 1/1993 | McCormick et al. |
| 5,242,418 A | 9/1993 | Weinstein |
| 5,256,152 A | 10/1993 | Marks |
| 5,271,070 A | 12/1993 | Truong et al. |
| 5,295,972 A | 3/1994 | Mischenko |
| 5,328,483 A | 7/1994 | Jacoby |
| 5,334,155 A | 8/1994 | Sobel |
| 5,549,571 A | 8/1996 | Sak |
| 5,562,633 A | 10/1996 | Wozencroft |
| 5,584,818 A | 12/1996 | Morrison |
| 5,630,803 A | 5/1997 | Tamaro |
| 5,688,241 A | 11/1997 | Asbaghi |
| 5,713,872 A | 2/1998 | Feuerborn et al. |
| 5,716,872 A | 2/1998 | Isobe |
| 5,735,827 A | 4/1998 | Adwers et al. |
| 5,738,665 A | 4/1998 | Caizza et al. |
| 5,755,699 A | 5/1998 | Blecher et al. |
| 5,817,070 A | 10/1998 | Tamaro |
| 5,833,670 A | 11/1998 | Dillon et al. |
| 5,893,845 A * | 4/1999 | Newby et al. .............. 604/198 |
| 5,951,525 A | 9/1999 | Thorne et al. |
| 6,224,576 B1 | 5/2001 | Thorne et al. |
| 6,254,577 B1 | 7/2001 | Huet |
| 6,261,264 B1 | 7/2001 | Tamaro |
| 6,375,640 B1 | 4/2002 | Teraoka |
| 6,409,706 B1 | 6/2002 | Loy |

FOREIGN PATENT DOCUMENTS

| | | |
|---|---|---|
| EP | 0 713 710 A1 | 11/1995 |
| EP | 1 132 103 A1 | 11/2000 |
| GB | 2 301 036 A | 11/1996 |
| WO | WO 94/19036 | 9/1994 |
| WO | WO 03/026731 | 4/2003 |

* cited by examiner

Primary Examiner—Brian L. Casler
Assistant Examiner—Catherine S. Williams

(57) ABSTRACT

A needle assembly includes a tube holder for receiving an evacuated fluid collection tube. A needle cannula projects distally from said tube holder and a tip guard is slidably movable along said needle cannula from a proximal position near said tube holder to a distal position for shielding the distal end of the cannula. An actuator arm extends proximally from said tip guard and releasably engages the holder when the tip guard is in the proximal position. Insertion of a tube into the tube holder releases the actuator arm and enables the tip guard to be propelled to the distal position.

17 Claims, 19 Drawing Sheets

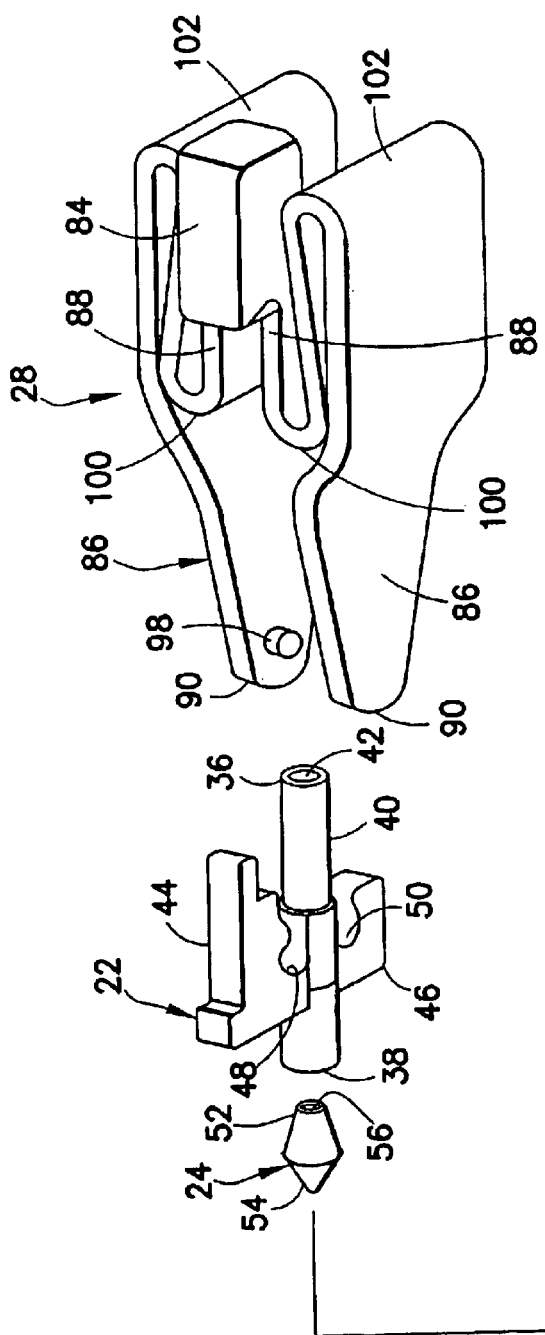
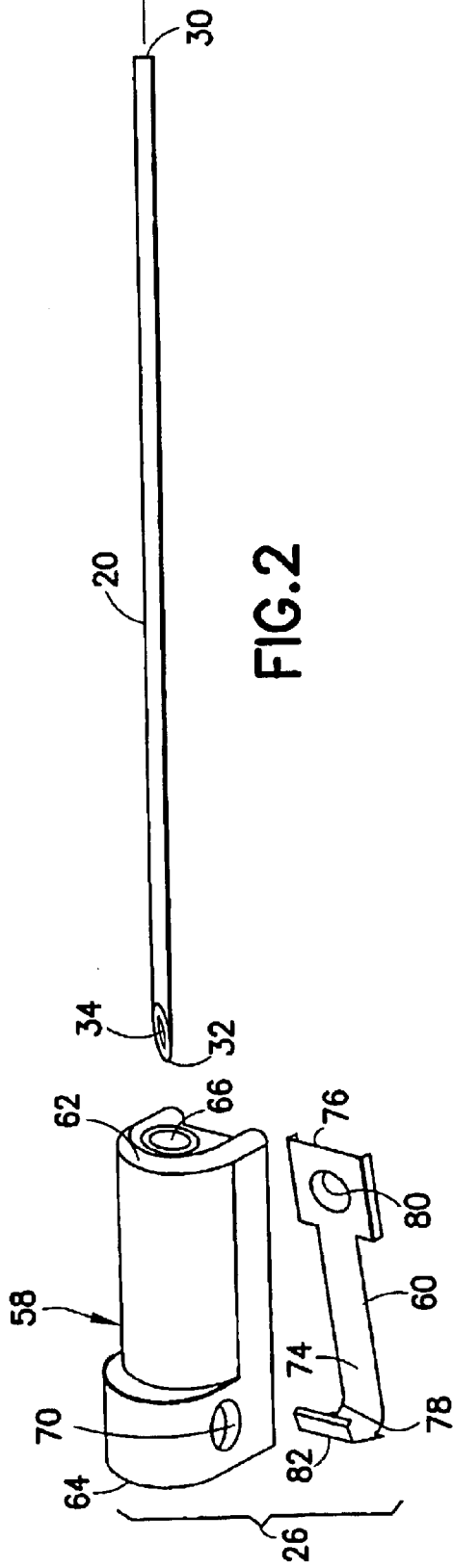
FIG.2

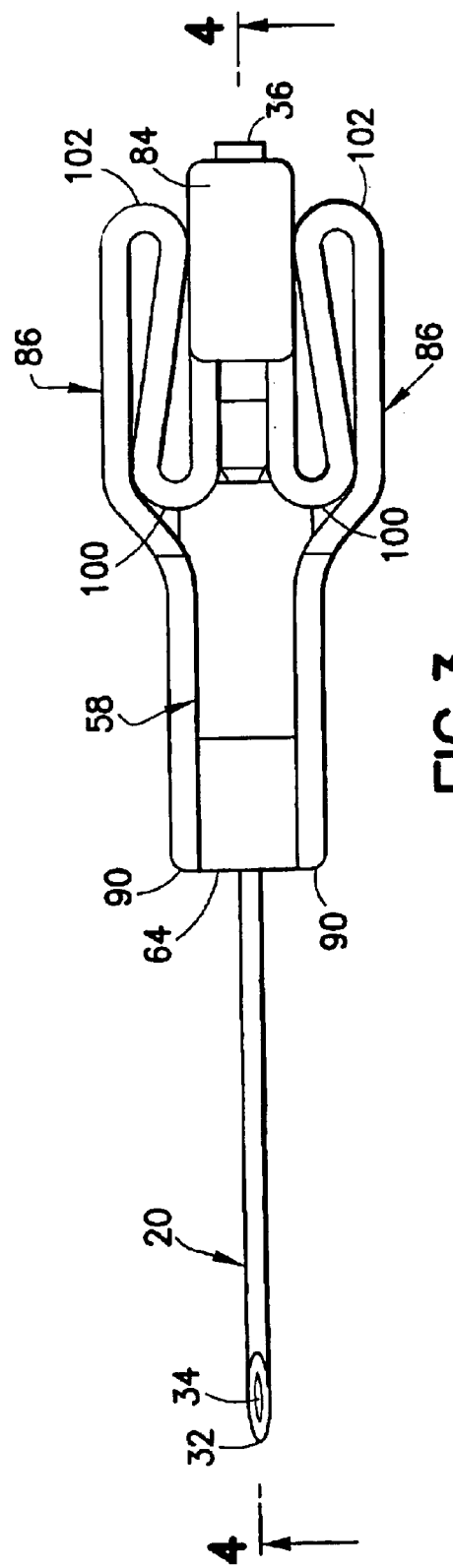
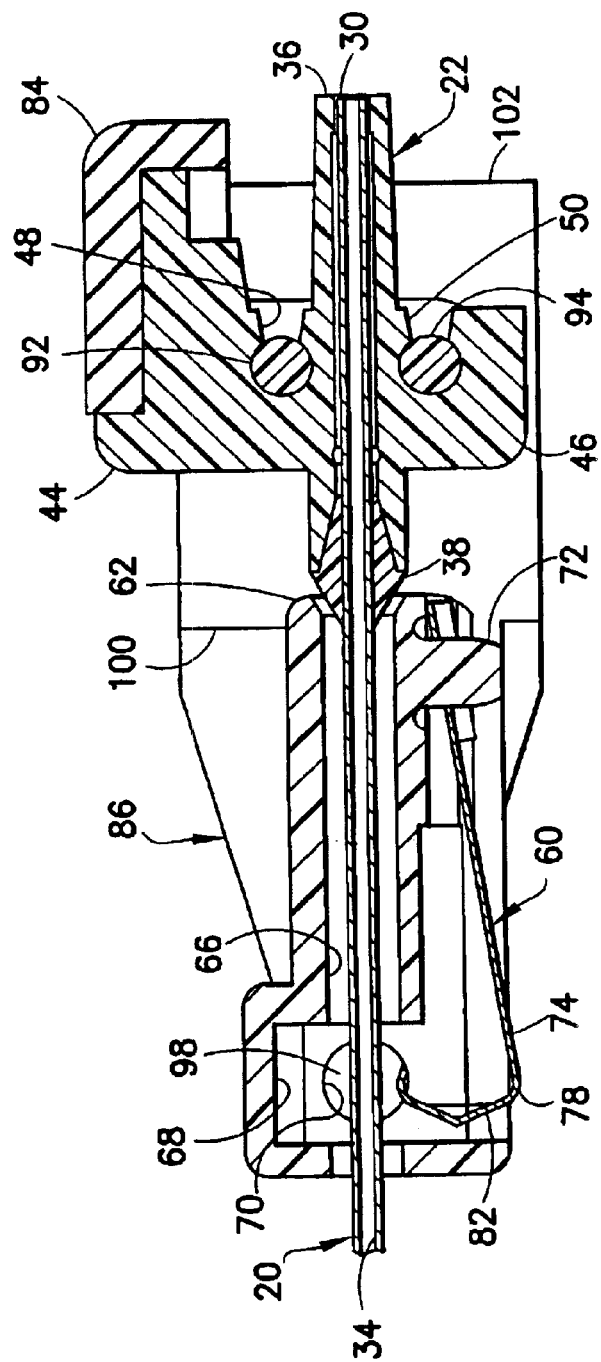

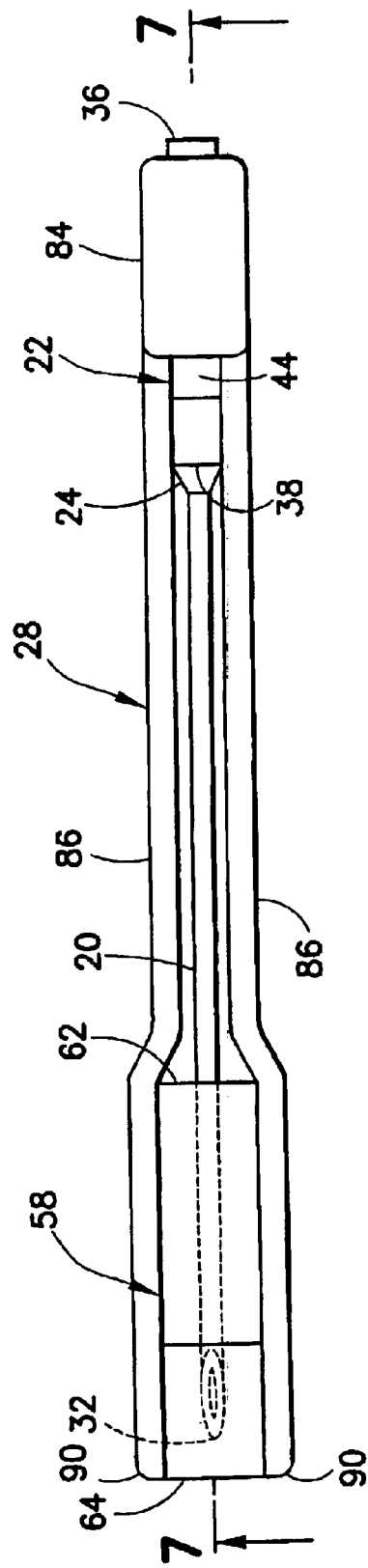
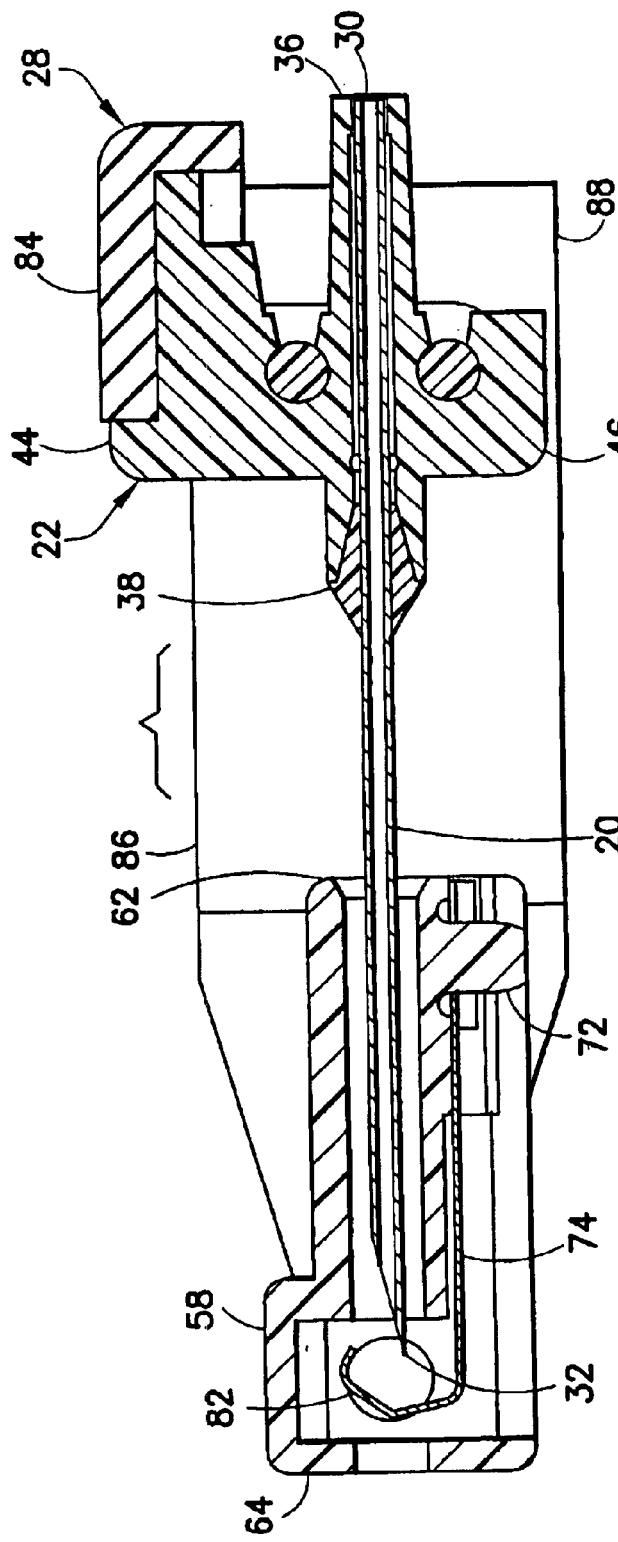

PASSIVE SAFETY DEVICE FOR NEEDLE OF BLOOD COLLECTION SET

RELATED APPLICATIONS

This application is a continuation-in-part application of pending U.S. patent application Ser. No. 10/370,924, filed on Feb. 20, 2003, which in turn was a continuation-in-part of U.S. patent application Ser. No. 09/521,078, filed Mar. 7, 2000, now patented U.S. Pat. No. 6,537,259, issued on Mar. 25, 2003.

BACKGROUND OF THE INVENTION

1. Field of the Invention

The subject invention relates to a passively activated safety shield for a needle, such as the needle for a fluid collection tube holder.

2. Description of the Related Art

A prior art blood collection set or IV infusion set includes a needle cannula having a proximal end, a pointed distal end and a lumen extending between the ends. The proximal end of the needle cannula is securely mounted in a plastic hub with a central passage that communicates with the lumen through the needle cannula. Thin flexible thermoplastic tubing is connected to the hub and communicates with the lumen of the needle cannula. The end of the tubing remote from the needle cannula may include a fixture for connecting the needle cannula to a blood collection tube or some other receptacle. The specific construction of the fixture will depend upon the characteristics of the receptacle to which the fixture will be connected.

Some fluid collection procedures employ a rigid blood collection holder instead of the above-described blood collection set. The tube holder includes a proximal end, a distal end and a tubular side wall extending between the ends. The proximal end of the holder is widely open and defines an entrance to a tube receptacle within the tubular side wall. A distal end wall extends partly across the distal end of the holder and has a mounting aperture that communicates with the tube receptacle. The mounting aperture in the distal end wall may include internal threads, movable jaws or similar structure for releasably receiving a needle assembly. The needle assembly includes a rigid plastic hub configured for releasable engagement with structure at the mounting aperture in the distal end wall of the holder. The needle assembly further includes a non-patient cannula that extends proximally from the hub and an IV cannula that extends distally from the hub. The non-patient cannula typically is covered by an elastomeric multiple sample sleeve and projects into the receptacle of the holder when the hub of the needle assembly is engaged with the threads or other structure at the mounting aperture in the distal end wall of the tube holder. The proximally extending non-patient cannula and the distally extending IV cannula typically are covered by separate packaging covers prior to use.

The needle assembly, tube holder and evacuated tube are employed by first removing the packaging cover over the non-patient cannula and engaging the hub in the mounting aperture in the distal end wall of the tube holder. Thus, the non-patient cannula projects into the holder. The packaging shield over the IV cannula then is removed and the pointed distal end of the IV cannula is used to access a blood vessel or other source of bodily fluid to be tested. The evacuated tube then is urged into the open proximal end of the holder so that the non-patient cannula pierces the rubber closure of the evacuated tube. The pressure differential will cause blood or other bodily fluid to flow into the evacuated tube. The evacuated tube will be separated from the needle holder after sufficient blood or other bodily fluid has been collected. Additional evacuated tubes then can be inserted into the holder for collecting further samples. The IV cannula is withdrawn from the patient after a sufficient number of samples have been collected.

Accidental sticks with a needle are painful and can lead to infection. Additionally, an accidental stick with a used needle can transmit disease. Accordingly, most prior art needle assemblies are provided with some form of shield to minimize the risk of an accidental needle stick. For example, prior art needle assemblies typically are provided with a packaging cover mounted over the needle cannula prior to use. The prior art packaging cover is frictionally engaged with the needle hub and can be removed immediately prior to using the needle assembly. Reshielding the used needle cannula with the original packaging cover would require the medical practitioner to hold the needle assembly in one hand and to move the point of the used needle cannula toward the hand in which the packaging cover is held. This reshielding procedure can lead to the accidental needle stick that the medical practitioner is trying to avoid. Accordingly, manufacturers of needle assemblies discourage medical practitioners from reshielding the used needle cannula with the original packaging cover.

Most prior art needle assemblies include a safety shield that can be moved into shielding engagement with a used needle cannula without risking an accidental needle stick. For example, some prior art needle assemblies include a needle shield hingedly connected to the needle hub. The hinged shield initially may be in a position that is spaced angularly from the needle cannula. However, the shield can be rotated relative to the needle hub and into shielding engagement around the used needle cannula. Digital forces for rotating this prior art hinged safety shield typically can be applied at a location near the needle hub and spaced from the pointed end of the needle cannula. As a result, shielding can be carried out manually without placing a hand near the point of the used needle cannula.

Other prior art safety shields include a rigid tubular member that is telescoped over the needle hub and/or over any medical device to which the needle assembly is mounted. The rigid safety shield can be moved from a proximal position where the needle cannula is exposed, into a distal position where the safety shield surrounds the used needle cannula. This shielding operation typically can be completed without placing a hand near the tip of the used needle cannula.

Some needle shields are referred to as tip guards, and include a small rigid guard that can be telescoped along the length of a needle cannula. The prior art tip guard may include some form of tether for limiting the travel of the tip guard to the length of the needle cannula. Additionally, the prior art tip guard typically includes structure that lockingly engages over the tip of the used needle cannula to prevent a re-exposure. The structure for preventing re-exposure may include a metallic spring clip or a transverse wall integrally formed with one end of the tip guard.

Some prior art needle assemblies are provided with metallic coil springs between the needle hub and the safety shield. A latch typically is provided for retaining the spring in a compressed state prior to and during use of the needle cannula. The latch is released upon removal of the needle cannula from the patient, and the spring then drives the shield distally and into shielding engagement with the needle cannula. Needle cannulas for blood collection sets and IV infusion sets typically are very small. Accordingly, the latches and the springs also must be very small. As a result, it often is difficult to access and release the latch. Furthermore, there is a significant potential for unreliable performance of the very small coil spring that had been stored in a compressed state for a long time.

All of the above described prior art shields for used needle cannulas require direct manual activation by the medical practitioner. The practitioner, however, often has many simultaneous responsibilities in the hectic environment of a health care facility. Thus, the used needle cannula may be withdrawn from a patient and deposited on a nearby surface with the intention of completing the shielding at a more convenient time. However, the exposed used needle cannula creates a substantial risk prior to completion of the shielding. Furthermore, there are many occasions where the needle of a blood collection set or an IV infusion set is pulled out, intentionally or unintentionally, by a patient. In this situation, shielding will not have been attempted, and the used needle cannula will remain exposed. In still other instances, the medical practitioner will inadvertently drop the used needle cannula immediately after withdrawal from the patient or during a shielding attempt. The immediate reaction of many medical practitioners will be to reach quickly for the falling needle cannula. This attempt to retrieve the falling needle cannula creates a significant possibility for an accidental needle stick.

Efforts have been made to develop a completely passive shielding assembly for use with a fluid collection tube holder, such as the holder for receiving an evacuated tube during a blood collection procedure. Some such devices include complex arrangements of springs and latches.

In view of the above, it is an object of the subject invention to provide a passively shieldable needle assembly that will reliably achieve secure shielding of a used needle cannula automatically upon removal of the needle cannula from the patient and without requiring special manipulation by a user.

SUMMARY OF THE INVENTION

One aspect of the invention is directed to a passively shieldable needle set. The needle set includes a needle cannula having a proximal end, a pointed distal end and a lumen extending between the ends. The needle set further comprises a hub having a proximal end, a distal end and a passage extending between the ends. The proximal end of the needle cannula is securely mounted in the passage of the hub. Flexible tubing may be mounted to the proximal end of the hub such that the passage through the tubing communicates with the lumen of the needle cannula. A fixture may be mounted to the end of the tubing remote from the hub. The fixture enables the needle cannula and the tubing to be placed in communication with an appropriate receptacle, such as a blood collection tube.

The needle set further includes a passive shield assembly. The shield assembly includes a tip guard that is telescoped on the needle cannula for sliding movement from a proximal position where the tip guard is substantially adjacent the hub to a distal position where the tip guard surrounds the pointed distal end of the needle cannula. Additionally, the tip guard may be configured to prevent a return proximal movement after the tip guard has advanced sufficiently in a distal direction to protectively enclose the distal tip of the needle cannula.

The tip guard may comprise a housing and a protective clip, each of which is formed from a material that is sufficiently hard and rigid to prevent piercing by the distal tip of the needle cannula. The housing may be formed from a thermoplastic material, and the clip may be formed from a metallic material. The clip is configured to be biased against the needle cannula as the tip guard moves from its proximal position toward the distal position. However, the clip is further configured to move over the tip of the needle cannula when the tip guard is in its distal position.

The passive shield assembly further includes a pair of resiliently deflectable leaves. The leaves have proximal ends that are connected to opposite respective sides of the hub. The leaves further have distal ends connected to opposite sides of the tip guard. A portion of each leaf between the ends is resiliently collapsible onto itself and into close overlying relationship to the needle hub. Thus, the collapsed leaves can be gripped manually by the medical practitioner to manipulate the needle assembly prior to and during veinipuncture. However, a release of forces on the collapsed leaves enables the leaves to resiliently move toward an undeflected condition in which the leaves extend substantially linearly and parallel to one another on opposed sides of the needle cannula. This resilient unfolding of the leaves transports the tip guard distally along the needle cannula. The leaves have lengths sufficient to enable the tip guard to move into shielding engagement with the tip of the needle cannula, without moving distally beyond the needle cannula.

The needle set further includes a packaging cover having an open proximal end, a distal end and a generally tubular sidewall extending therebetween. Portions of the sidewall of the packaging cover adjacent the open proximal end are configured to be mounted frictionally over the hub and over the collapsed leaves. Thus, the packaging cover functions to hold the leaves in their collapsed condition. The sidewall of the packaging cover is sufficiently long to cover the needle cannula when the proximal end of the packaging cover is mounted to the hub.

A medical practitioner employs the needle set of the subject invention by gripping the collapsed leaves of the shield assembly between a thumb and forefinger at a location proximally of the packaging cover. The packaging cover then is removed, and the tip of the needle cannula is inserted into a blood vessel of a patient. Upon completion of the insertion, the medical practitioner releases the grip on the collapsed leaves, and the leaves begin to unfold due to their inherent resiliency. The unfolding of the leaves causes the tip guard to move distally along the needle cannula. The distal movement of the tip guard will terminate when the tip guard contacts the skin of the patient. After completion of the medical procedure, the practitioner grabs the needle hub with a thumb and forefinger and pulls the needle cannula from the patient. This relative proximal movement of the needle cannula permits the leaves to unfold further, thereby moving the tip guard into surrounding relationship to the tip of the needle cannula. The clip or other such structure within the tip guard prevents a re-exposure of the used needle cannula.

It will be appreciated that the shield assembly is triggered by the medical practitioner, but shielding is entirely passive and automatic after the triggering. The triggering action is the release of the collapsed leaves by the medical practitioner. This release can occur after the needle cannula has been placed properly in a blood vessel. Alternatively, this triggering can occur if the needle set is inadvertently dropped. The elapsed time for this shielding will vary depending upon the characteristics of the leaves. Typically, however, complete shielding can occur before a dropped needle has fallen one foot.

Another aspect of the invention relates to a passively shieldable needle assembly. The needle assembly includes a needle cannula having a pointed proximal end, a pointed distal end and a lumen extending between the ends. The needle assembly further comprises a hub having a proximal end, a distal end and a passage extending between the ends. Portions of the needle cannula between the pointed proximal and distal ends are mounted securely in the passage of the hub. Thus, the pointed proximal end of the needle cannula projects proximally beyond the hub and the pointed distal end of the needle cannula projects distally beyond the hub. External surface regions of the hub near the proximal end of the hub may be formed with mounting structures, such as an array of external threads, at least one annular groove or at least one annular rib. The mounting structure enables the needle hub to be secured to a tube holder that is configured to slidably receive an evacuated fluid collection tube. The needle assembly may further include a multiple sample sleeve mounted over the proximal portions of the needle cannula and secured to the proximal end of the hub. The proximal portions of the needle cannula and the multiple sample sleeve project into the tube holder when the hub of the needle assembly is mounted to the holder.

The needle assembly further includes a passive shield assembly and a packaging cover substantially as described with respect to the first embodiment. However, the resiliently deflectable leaves of the passive shield assembly preferably are configured to project into partly overlying relationship with the tube holder when the needle assembly is mounted to the holder. Thus, portions of the collapsed leaves can be gripped manually by the medical practitioner simultaneously while gripping the tube holder for drawing blood or other bodily fluid from a patient. The packaging cover may be a distal packaging cover for covering the distal projection of the needle cannula beyond the hub and for holding the leaves in their collapsed condition. The needle assembly may further include a proximal packaging cover for covering the proximal projection of the needle cannula beyond the hub.

The needle assembly is employed by first removing the proximal packaging cover from the needle assembly and attaching the needle assembly to a tube holder. In this condition, portions of the collapsed leaves or extensions of the leaves are disposed on opposite sides of the holder. The medical practitioner grips these portions of the leaves that overlie the tube holder for securely gripping both the collapsed leaves and the holder. The distal packaging cover then is removed and the exposed distal point of the needle cannula is employed in a conventional manner to access a blood vessel. Immediately upon accessing the blood vessel, the medical practitioner shifts his or her grip on the tube holder so that the collapsed leaves are released. The leaves then begin to unfold due to their inherent resiliently, substantially as in the first embodiment. This unfolding of the leaves causes the tip guard to move distally along the needle cannula and into gentle contact with the skin of the patient. The medical practitioner then inserts an evacuated tube into the open proximal end of the tube holder so that the evacuated tube is urged into communication with the proximal end of the needle cannula. The pressure differential will generate a flow of blood into the evacuated tube. The evacuated tube is withdrawn from the holder after a sufficient volume of fluid has been collected, and one or more evacuated tubes may be inserted successively into the holder for drawing additional samples. After the last sample has been collected, the tube is withdrawn from the holder and the holder is pulled away from the patient. As a result, the leaves will unfold further and move the tip guard into surrounding relationship with the tip of the needle cannula as in the first embodiment.

Passive activation of the shield assembly can be triggered by insertion of a fluid collection tube into the tube holder to which the needle assembly is mounted. For example, the tube holder may include an actuator opening in the distal end wall of the tube holder at a location offset from the needle cannula. An actuator arm may be mounted or formed near the tip guard and may project proximally from the tip guard into and through the actuator opening of the tube holder when the tip guard is in its proximal position. The actuator arm may be formed with a locking structure that releasably engages a portion of the tube holder when the tip guard is in the proximal position. The actuator arm is disposed to be contacted by a fluid collection tube as the tube is inserted into the tube holder. Distal movement of the tube into the tube holder will disengage the locking structure on the actuator arm from the tube holder and will initiate the distal movement of the tip guard along the cannula. The leaves will resiliently unfold as in the prior embodiments, thereby propelling the tip guard initially into contact with the skin of the patient, and eventually into shielding relationship with respect to the pointed distal end of the needle cannula. As in the previous embodiments, the resilient leaves will unfold into a position where the leaves lie on opposite sides of the used needle cannula, and hence will prevent inadvertent contact with the needle cannula. Furthermore, the actuator arm will parallel the needle cannula and will further prevent inadvertent contact with the used needle cannula. As in other embodiments, the expanded leaves will prevent the tip guard from moving distally beyond the distal tip of the needle cannula.

BRIEF DESCRIPTION OF THE DRAWINGS

FIG. 2 is an exploded perspective view of the passively shieldable needle device of the blood collection set.

FIG. 3 is a top plan view of the passively shieldable needle device.

FIG. 4 is a cross-sectional view taken along line 4—4 in FIG. 3.

FIG. 6 is a top plan view of the shield assembly in the shielded condition.

FIG. 7 is a cross-sectional view taken along line 7—7 in FIG. 6.

DETAILED DESCRIPTION

Figure 1:
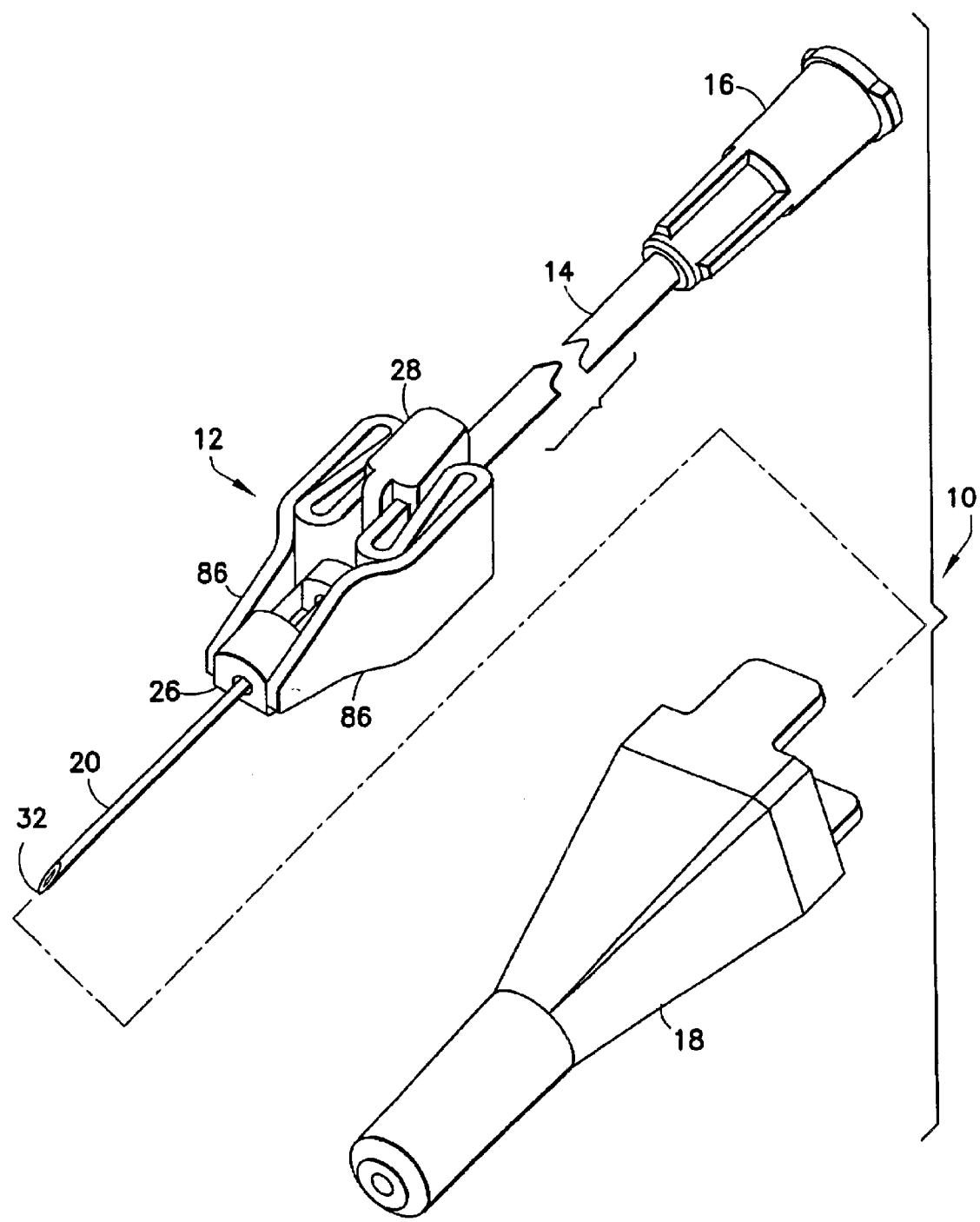
FIG. 1 is an exploded perspective view of a blood collection set in accordance with the subject invention.
Figure 5:
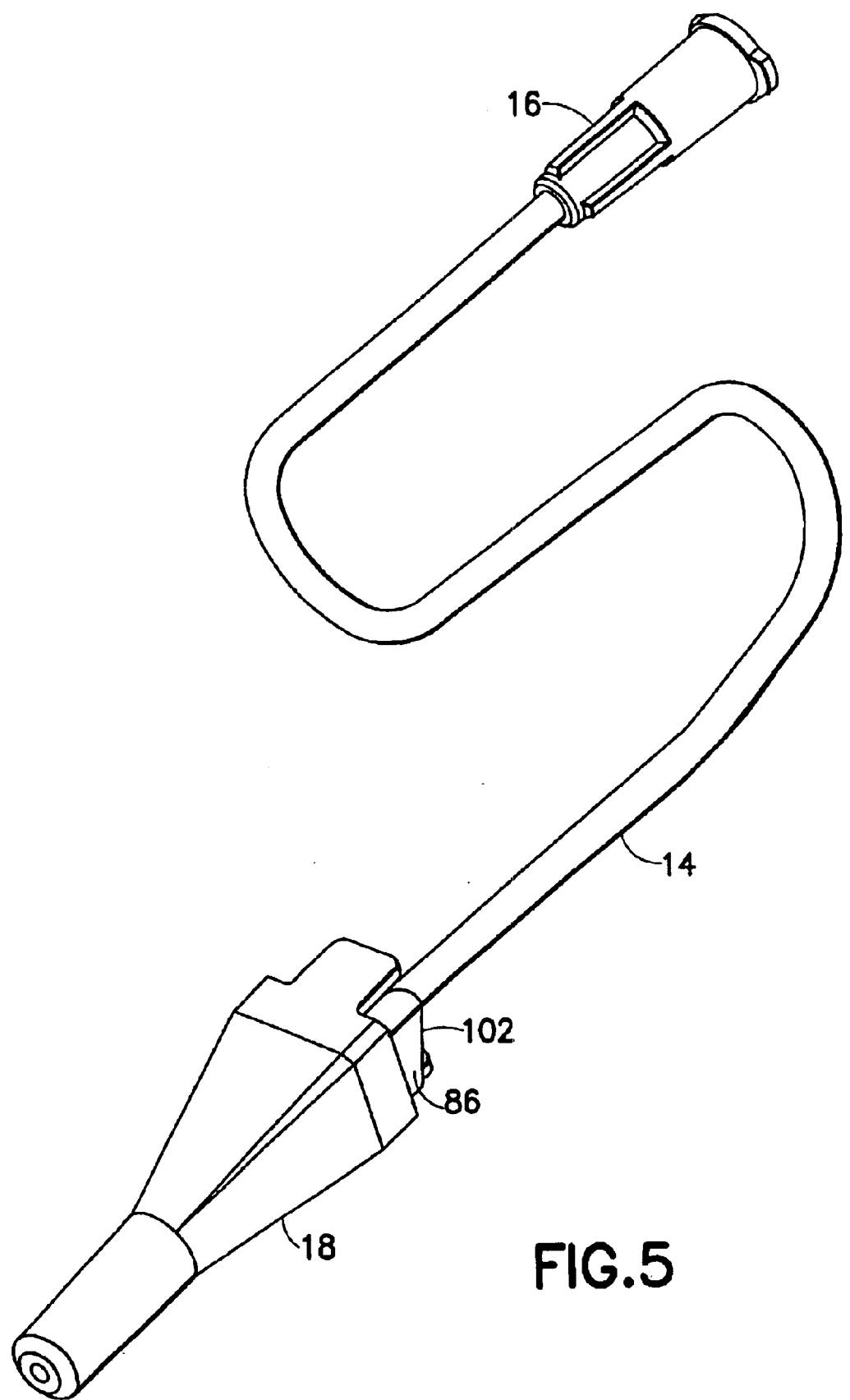
FIG. 5 is a perspective view of the fully assembled blood collection set with the packaging cover thereon.

A blood collection set in accordance with the subject invention is identified generally by the numeral 10 in FIGS. 1 and 5. Blood collection set 10 includes a passively shieldable needle device 12, a flexible tube 14 extending from needle device 12, a fixture 16 mounted to tube 14 and a packaging cover 18 removably mounted to portions of needle device 12 opposite tube 14.

Passively shieldable needle device 12 of blood collection set 10 is shown more clearly in FIGS. 2–4, and comprises a needle cannula 20, a hub 22, a collet 24, a tip guard assembly 26 and a collapsible guard drive 28. Needle cannula 20 includes a proximal end 30, a distal end 32 and a lumen 34 extending through cannula 20. Distal end 32 of needle cannula 32 is beveled to define a sharp tip.

Hub 22 is unitarily molded from a thermoplastic material and includes a proximal end 36, a distal end 38 and a rigid tube 40 extending between the ends. Rigid tube 40 is characterized by a passage 42 extending from proximal end 36 to distal end 38 of hub 22. Hub 22 further includes top and bottom flanges 44 and 46 extending oppositely in substantially coplanar relationship from a location on tube 40 approximately midway between proximal and distal ends 36 and 38. The terms top and bottom to identify flanges 44 and 46 are not intended to imply a required gravitational orientation, but do relate to a gravitational orientation that most commonly will be used with blood collection set 10, as dictated by the orientation of the bevel on needle cannula 20.

Top flange 44 of hub 22 is provided with a locking recess 48 substantially adjacent tube 40. Locking recess 48 opens toward proximal end 36 of hub 22 and includes a cross-sectionally reduced entry to enable a snap fit retention of mounting pegs on collapsible guard drive 28, as explained further herein. Similarly, bottom flange 46 includes a locking recess 50 which opens toward proximal end 36 of hub 22 and which has a shape and size substantially identical to locking recess 48.

Collet 24 includes a proximal end 52, a distal end 54 and a passage 56 that is dimensioned to closely enagage the outer circumferential surface of needle cannula 20. Thus, needle cannula 20 can be slid through passage 56 of collet 24, and can be positioned in passage 42 of hub 22. Collet 24 then can be secured both to needle cannula 20 and to hub 22.

Tip guard assembly 26 includes a housing 58 and a protective clip 60. Housing 58 is unitarily molded from a thermoplastic material and includes a proximal end 62, a distal end 64 and a passage 66 extending between the ends. Portions of passage 66 near distal end 64 define an enlarged clip receptacle 68 as shown in FIG. 4. Symmetrically opposed leaf mounting apertures 70 extend through opposite sides of housing 58 at clip receptacle 68. Additionally, a clip mounting post 72 extends downwardly from housing 58 at a location near proximal end 62 of housing 58.

Clip 60 is unitarily stamped and formed from a resiliently deflectable metallic material. Clip 60 includes a planar spring leg 74 with a proximal end 76 and an opposed distal end 78. A mounting aperture 80 extends through spring leg 74 at a location near proximal end 76. Aperture 80 has a diameter approximately equal to or slightly less than the diameter of mounting post 72 of housing 58. Thus, mounting post 72 can be forced through mounting aperture 80 when the axis of mounting post 72 and the axis of mounting aperture 80 are substantially colinear. A lock out leg 82 extends angularly from distal end 78 of spring leg 74. Lock out leg 82 is bent back toward proximal end 76 of clip 60. The bends in lock out leg 82 enable secure protective engagement with distal tip 32 of needle cannula 20 and further enable smooth sliding movement of tip guard assembly 26 along needle cannula 20 as explained further herein.

Collapsible guard drive 28 includes a downwardly and distally opening mounting block 84 which is dimensioned to slidably engage portions of upper flange 44 of hub 22 furthest from tube 40. Collapsible guard drive 28 further includes a pair of substantially identical leaves 86 extending unitarily from mounting block 84. Each leaf 86 has a width several times greater than the width of needle cannula 20 and a length sufficient to permit shielding of distal end 32 of needle cannula 20 as explained below. Leaves 86 are formed from a resiliently deformable material, such as silicone, that is capable of collapsing onto itself for defining a plurality of folds. Each leaf 86 includes a proximal end 88 and a distal end 90. Proximal end 88 of each leaf 86 is formed with top and bottom locking projections 92 and 94 which extend toward the other of the opposed leaves 86 and which are dimensioned to be lockingly received in locking recesses 48 and 50 of hub 22. Each leaf 86 further includes a distal mounting projection 98 substantially adjacent distal end 90. Distal mounting projections 98 are dimensioned for locking engagement in apertures 70 of tip guard housing 58. Leaves 86 can be folded or collapsed onto themselves and into close overlying relationship with mounting block 84 of collapsible guard drive 28, as shown most clearly in FIG. 2. More particularly, the collapsed folding of each leaf 86 forms distal fold 100 and a proximal fold 102. Proximal folds 102 are disposed substantially in alignment with proximal end 36 of hub 12.

Tip guard assembly 26 is assembled by forcing mounting post 72 of tip guard housing 58 through aperture 80 of clip 60. Spring leg 74 of clip 60 then is urged downwardly or away from passage 66 through tip guard housing 58. Distal end 32 of needle cannula 20 then is urged into passage 66 at proximal end 62 of tip guard housing 58. The downward deflection of spring leg 74 enables distal end 32 of needle cannula 20 to be passed entirely through tip guard 58. Spring leg 74 can be released after tip 32 of needle cannula 20 passes through tip guard housing 58. Thus, the end of lock out leg 82 will be biased against and slide along needle cannula 20. Tip guard assembly 26 then is slid proximally along needle cannula 20 into a position adjacent hub 22.

Mounting block 84 of collapsible guard drive 28 is slid distally over proximal end of top flange 44 on hub 22. This distal movement of mounting block 84 causes projections 94 and 96 of leaves 86 to be lockingly engaged in locking recesses 48 and 50 of top and bottom flanges 44 and 46 respectively. Sufficiently distal force will ensure locked engagement of projections 94 and 96 in recesses 48 and 50 of hub 22. Leaves 86 then are collapsed onto themselves as shown in FIGS. 2 and 3 to form distal folds 100 and proximal folds 102. In this collapsed condition, projections 98 on leaves 86 can be aligned with and lockingly engaged in apertures 70 of tip guard housing 58. Leaves 86 are retained in this collapsed condition and packaging cover 18 then is urged proximally over needle cannula 20. With reference to FIG. 1, packaging cover 18 includes an open proximal end configured for frictional engagement over hub 22 and over most of collapsible guard drive 28. However, portions of collapsed leaves 86 adjacent proximal folds 102 are maintained in an exposed state. In this fully mounted condition, distal dip 32 of needle cannula 20 is safely disposed within packaging cover 18.

Blood collection set 10 can be packaged substantially in the condition shown in FIG. 5. Prior to use, blood collection set 10 is removed from its package. Fixture 16 then may be connected to an appropriate receptacle for providing communication to lumen 34 through needle cannula 20.

To place needle cannula 20 in communication with a blood vessel, a medical practitioner manually engages proximal folds 102 of leaves 86 at the exposed portions on opposite sides of packaging cover 18. Packaging cover 18 then is urged distally to disengage packaging cover 18 from needle device 12. The medical practitioner then can urge the tip at pointed distal end 32 of needle cannula 20 into a targeted blood vessel of a patient, while continuing to hold collapsed leaves 86 adjacent proximal folds 102 between a thumb and forefinger. After the targeted blood vessel has been accessed, the medical practitioner can release the grip on leaves 86. The inherent resiliency of collapsible guard drive 28 will cause leaves 86 to automatically unfold, thereby propelling tip guard assembly 26 distally along needle cannula 20. Distal movement of tip guard assembly 26 will terminate when proximal end 64 of tip guard housing 58 contacts the skin of the patient near the puncture site.

Upon completion of the required medical procedure, needle cannula 20 is withdrawn from the patient. This removal of needle cannula 20 from the patient will permit further unfolding of leaves 86 and a corresponding distal movement of tip guard assembly 26. After sufficient distal movement of tip guard assembly 26, lockout leg 82 of clip 60 will pass distally beyond tip 32 of needle cannula 20. The inherent resiliency of spring leg 74 of clip 60 will urge lockout leg 82 over tip 32 of needle cannula 20. Thus, a return movement of tip guard assembly 26 that would re-expose the used needle cannula is prevented. Furthermore, leaves 86 have overall length dimensions that will prevent movement of tip guard assembly 26 distally beyond needle cannula 20. Hence, tip 32 of needle cannula 20 is safely shielded. Furthermore, inadvertent contact with portions of needle cannula 20 between the opposed end is substantially prevented by the considerable width of leaves 86 compared to needle cannula, as shown most clearly in FIGS. 6 and 7.

As explained above, the combination of collapsible guard drive 28 and tip guard assembly 26 enables automatic passive shielding of needle cannula 20 merely by removing needle cannula 20 from the patient. In some instances, however, needle device 12 may be dropped or knocked from the hand of the medical practitioner either before veinipuncture or during a medical procedure. The passive shielding described above will commence automatically when needle device 12 is dropped or knocked from the medical practitioner's hand. Thus, the automatic shielding may be triggered by the intentional or unintentional release of the collapsed leaves 86 by the medical practitioner. The speed for this automatic passive shielding will vary in accordance with the materials from which leaves 86 are formed. However, a typical shielding can be completed before needle device 12 falls one foot under the action of gravity.

A medical practitioner does not always enter the targeted blood vessel during the first veinipuncture attempt. However, a medical practitioner typically retains a close grip on the needle device until the targeted blood vessel has been entered. In this instance, the continued gripping of the collapsed leaves 86 will prevent the needle from shielding until the targeted blood vessel has been punctured. The second attempt at accessing a targeted blood vessel generally is a very low risk procedure in which the practitioner's hand is spaced considerably from the tip 32 of needle cannula 20. Thus, blood collection set 10 does not involve the inconvenience of having to use a new blood collection set following each unsuccessful veinipuncture attempt.

Figure 8:
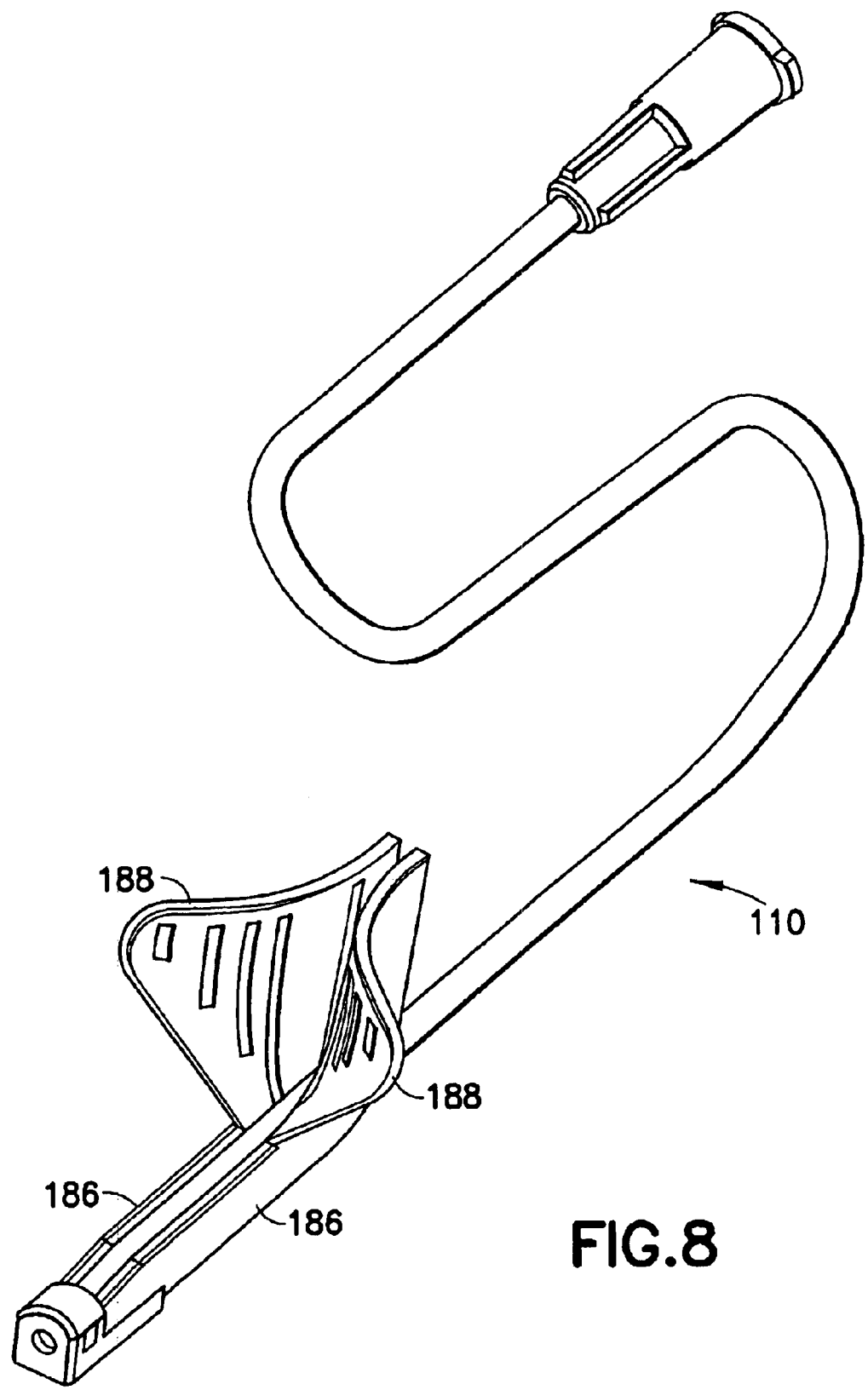
FIG. 8 is a perspective view of a blood collection set showing a second shield assembly in shielding engagement around a needle cannula.
Figure 9:
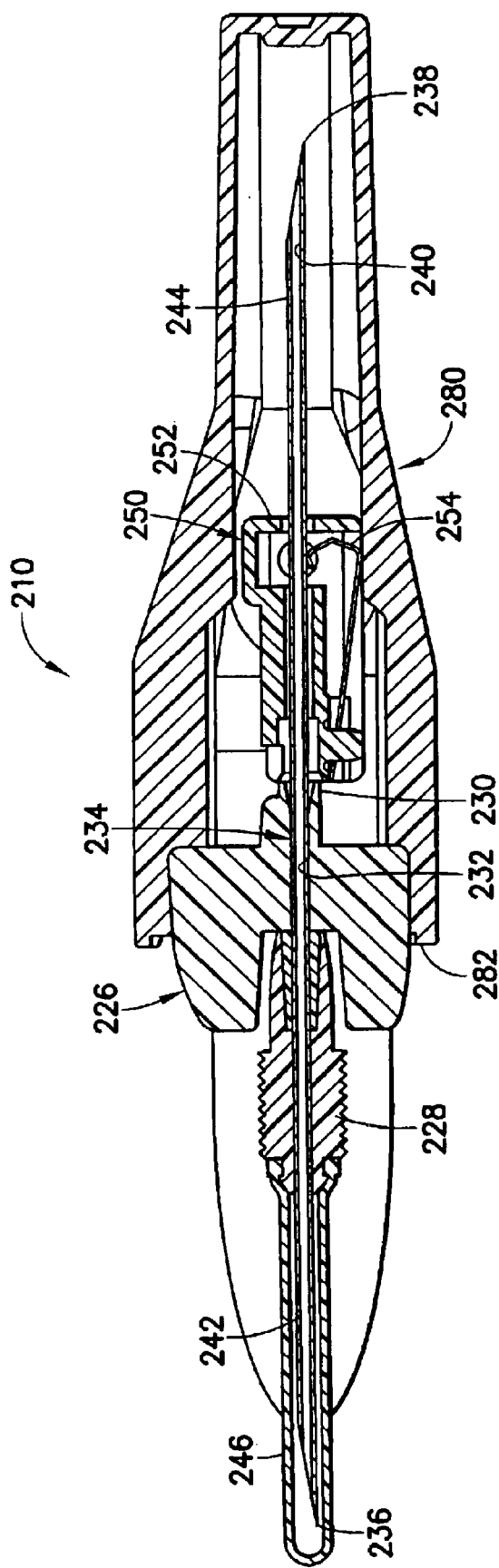
FIG. 9 is a longitudinal cross-sectional view of a needle assembly in accordance with a third embodiment of the invention.
Figure 10:
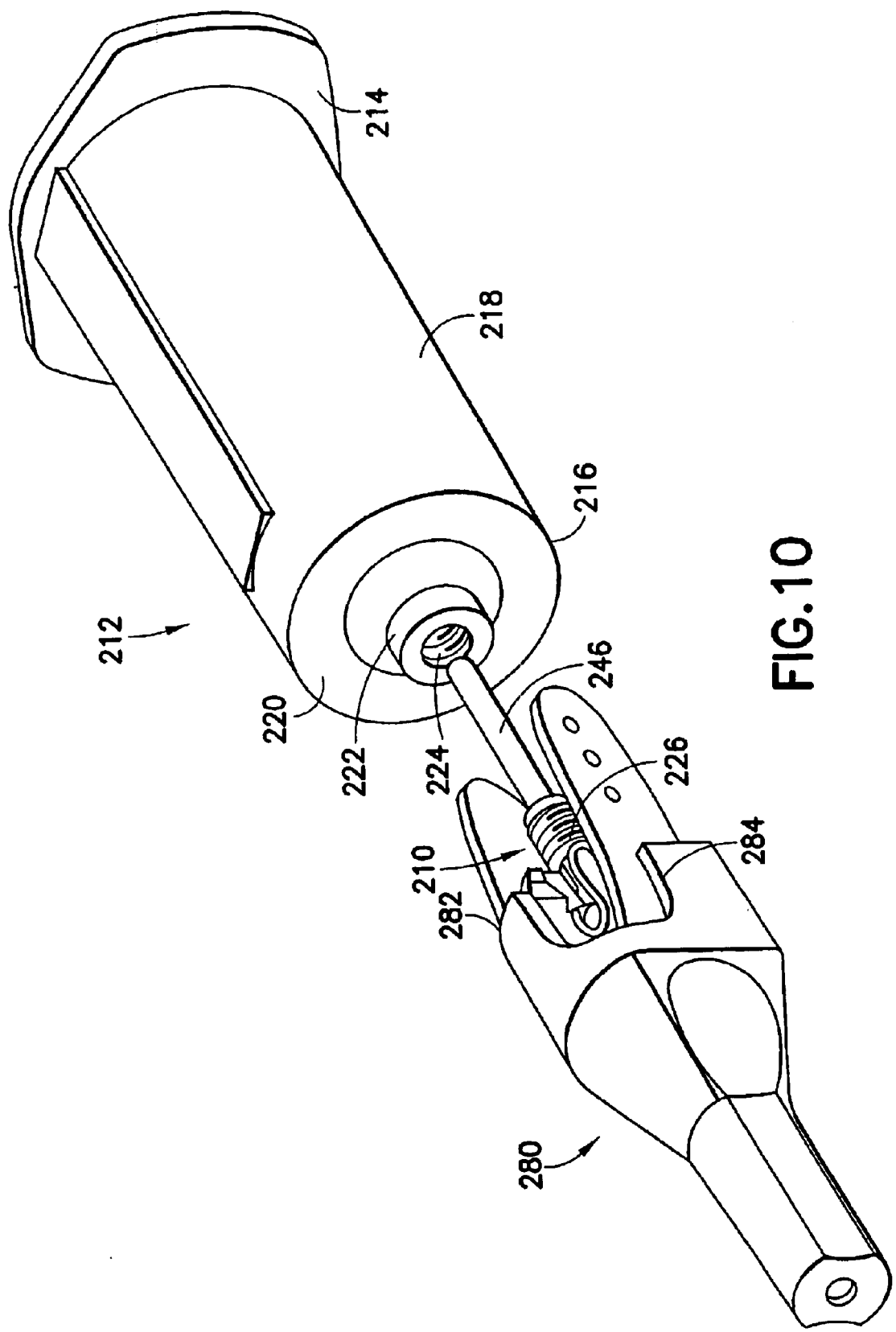
FIG. 10 is an exploded perspective view of the needle assembly of FIG. 9 in proximity to a tube holder.

FIG. 8 shows an alternate blood collection set 110. Blood collection set 110 is substantially identical to blood collection set 10 described above. However, leaves 186 of blood collection set 110 include wings 188 projecting therefrom. Additionally, a packaging cover used with blood collection set 110 is configured to accommodate wings 188. Wings 188 can facilitate digital manipulation of the shieldable needle device of blood collection set 110.

Figure 11:
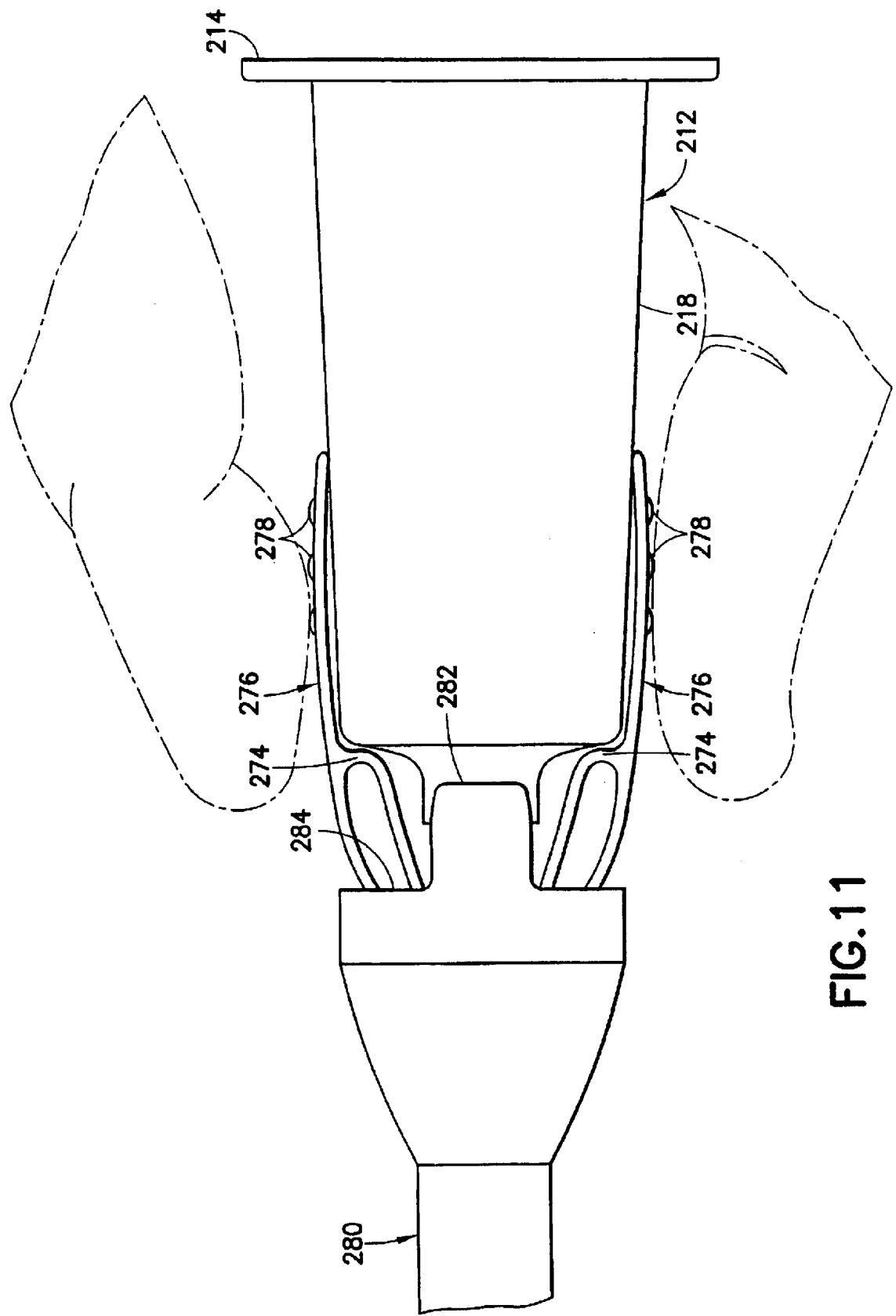
FIG. 11 is a top plan view of the needle assembly mounted to the tube holder.
Figure 12:
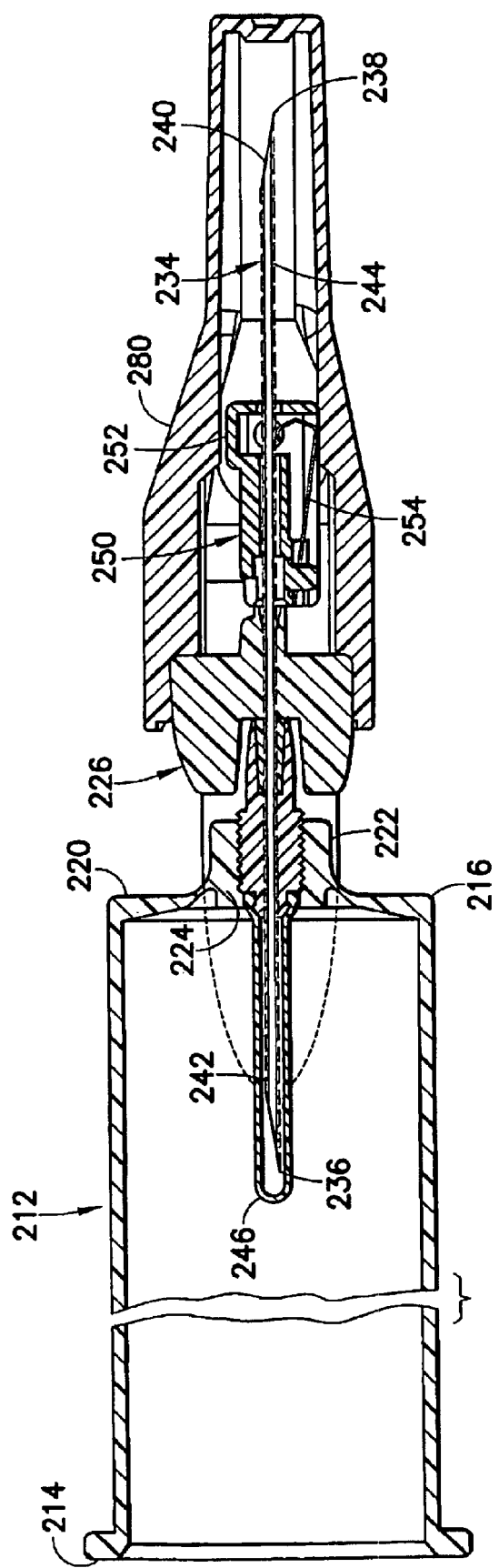
FIG. 12 is a cross-sectional view taken along line 12—12 in FIG. 11.
Figure 13:
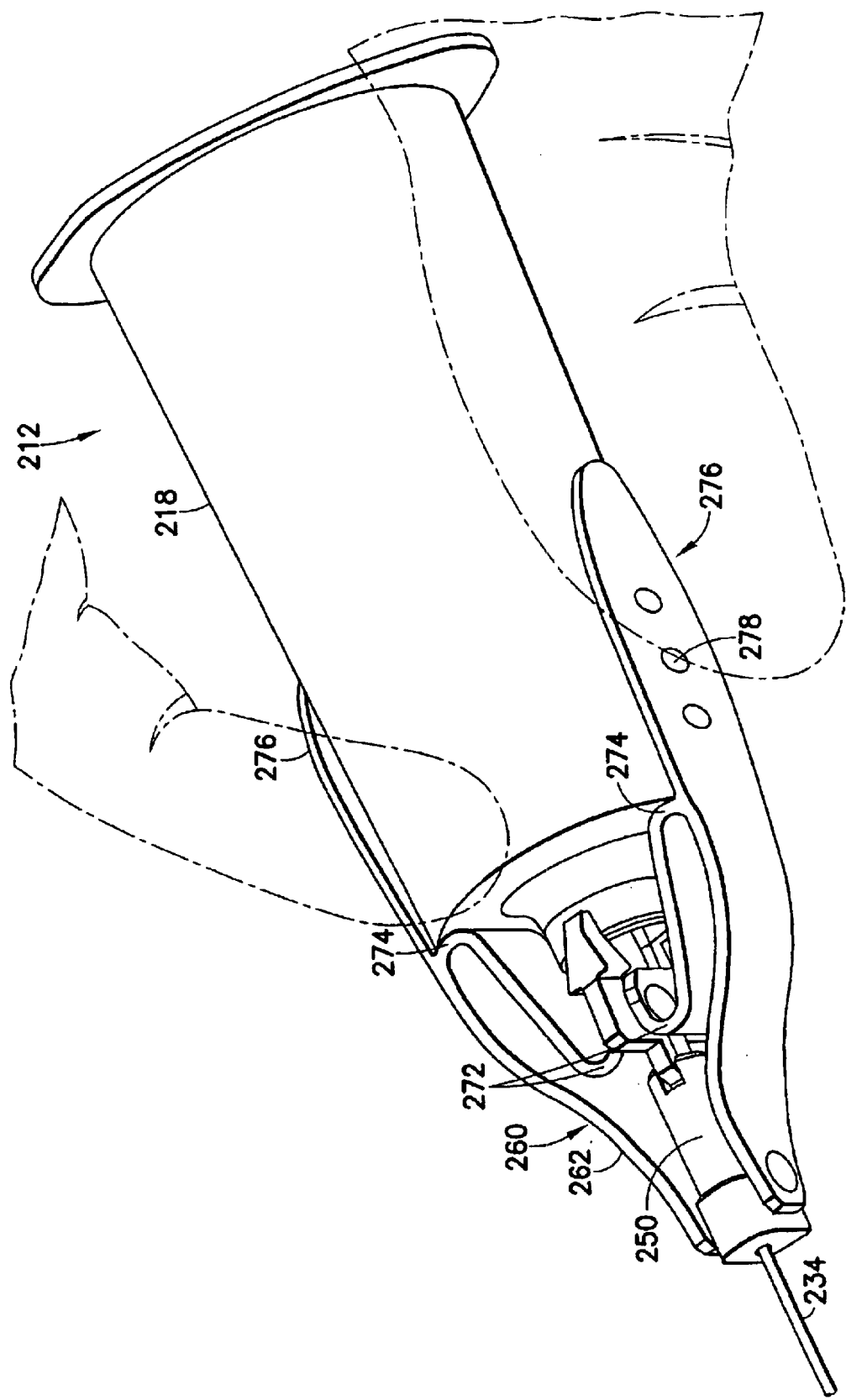
FIG. 13 is a perspective view showing the distal packaging cover removed from the needle assembly.
Figure 14:
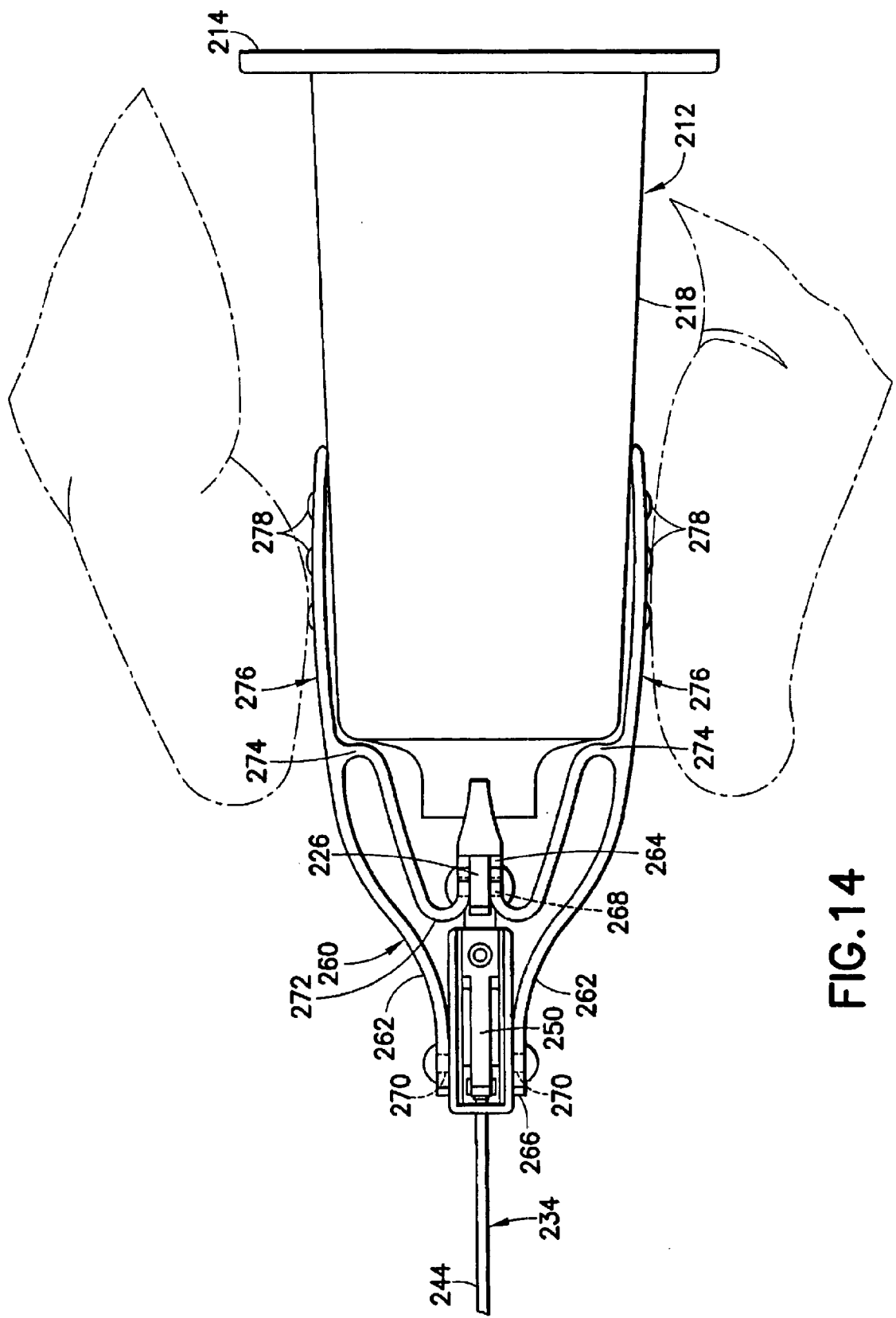
FIG. 14 is a top plan view of the needle assembly and tube holder immediately prior to use.
Figure 15:
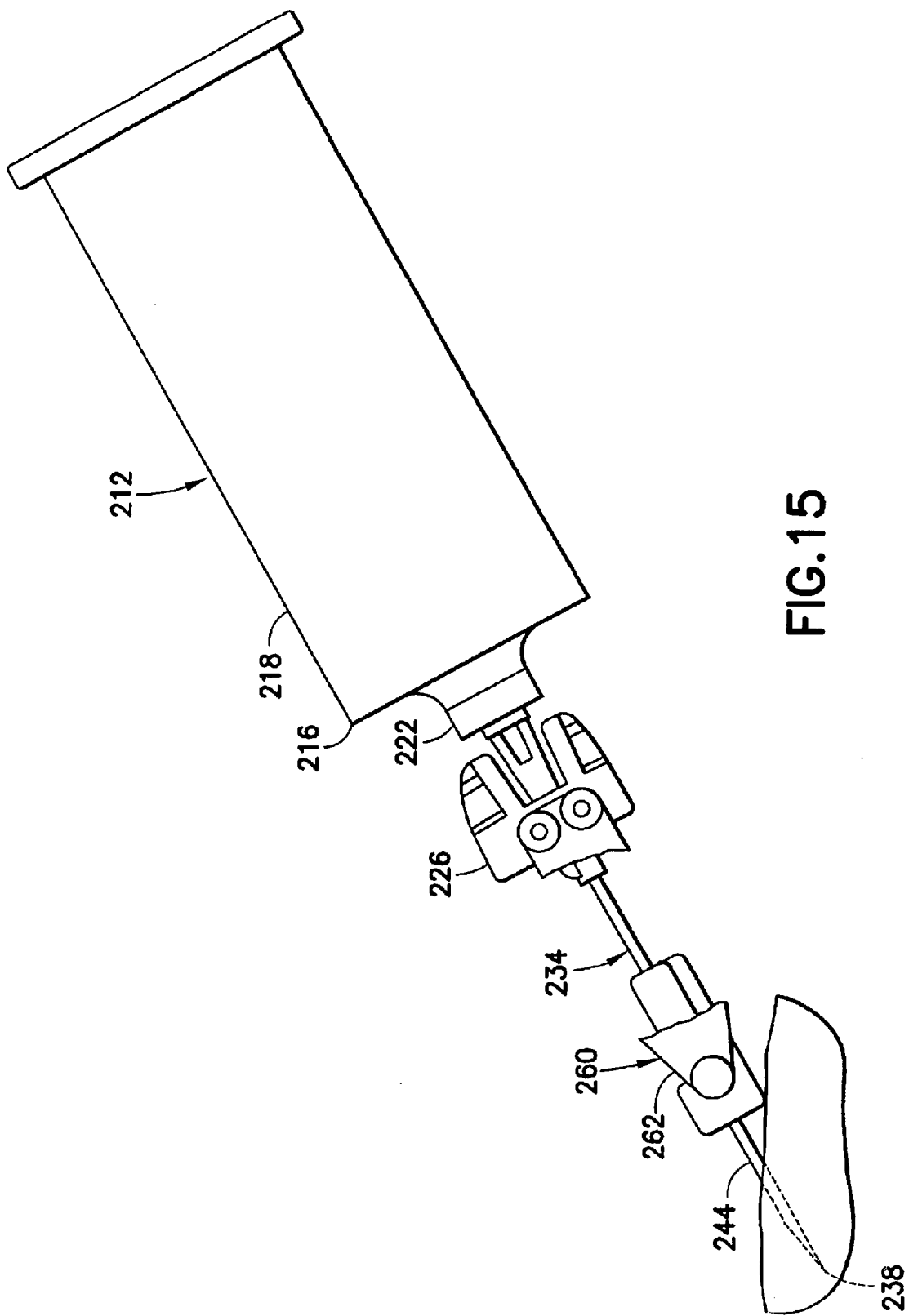
FIG. 15 is a side elevational view of the needle assembly and tube holder during use.
Figure 16:
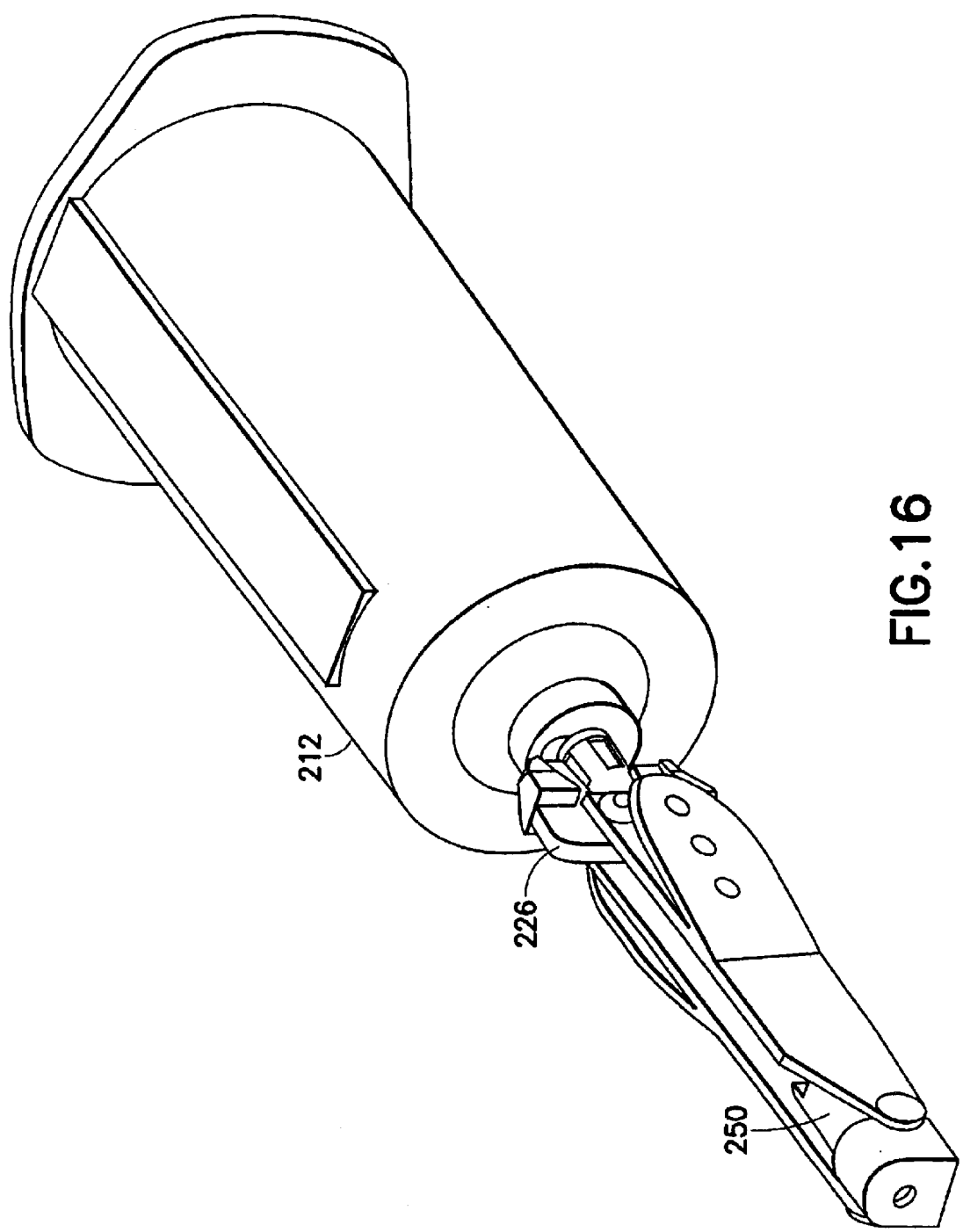
FIG. 16 is a perspective view of the tube needle assembly and tube holder after use and with the needle cannula fully shielded.
Figure 17:
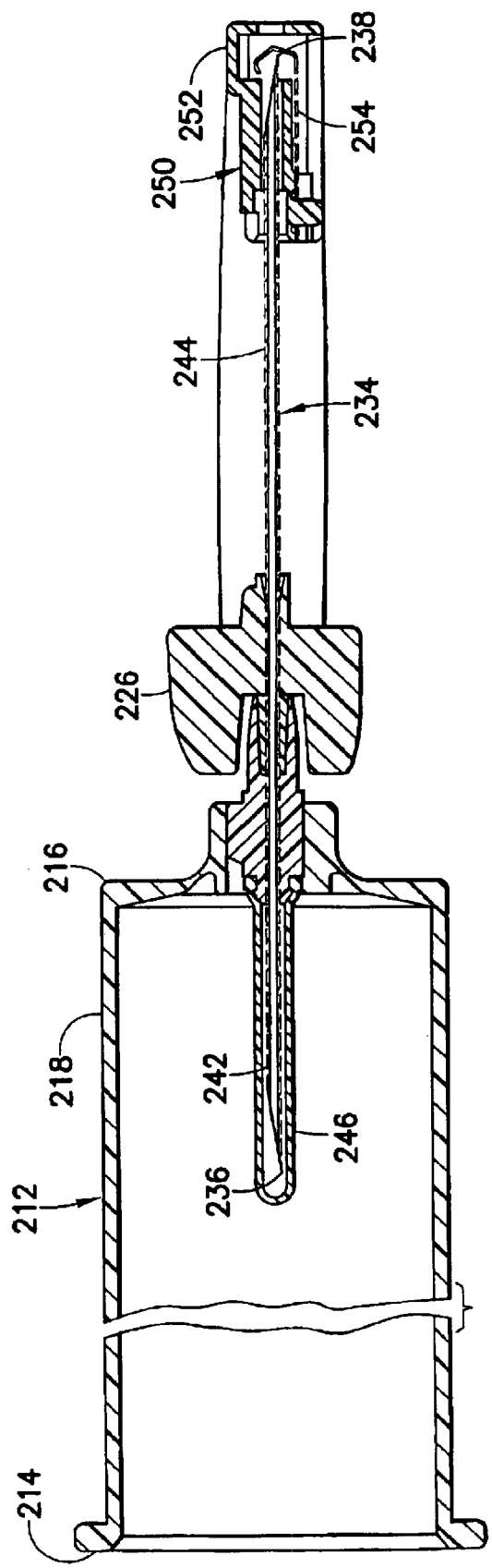
FIG. 17 is a cross-sectional view taken along line 17—17 in FIG. 16.

FIGS. 9–17 show a blood collection needle assembly 210 according to a third embodiment of the invention and adapted for use with a tube holder. Holder 212 includes a proximal end 214, a distal end 216 and a tubular sidewall 218 extending between the ends. Proximal end 214 is widely open, as shown in FIGS. 12 and 17, and is configured for slidably receiving an evacuated tube, such as the VACU-TAINER® brand of evacuated tubes sold by Becton Dickinson and Company. Distal end 216 of holder 212 includes an end wall 220 that extends in from tubular sidewall 218. End wall 220 includes a mounting collar 222 with a mounting aperture 224 for receiving needle assembly 210, as described below. Mounting aperture 220 is provided with structure for releasably engaging needle assembly 210. As illustrated herein, mounting aperture 224 of mounting collar 220 is configured for a threaded connection. However, other embodiments may have other mounting structures, such as grooves, ribs or a bayonet connection. Still other arrangements may include an assembly of movable jaws for releasably gripping needle assembly 210.

Needle assembly 210 includes a hub 226 with a proximal end 228, a distal end 230 and a passage 232 extending between the ends. Proximal end 228 of hub 226 is formed with an array of external threads for engaging the threads of mounting aperture 224 in holder 212. Needle assembly 210 further includes a needle cannula 234 that has a pointed proximal end 236, a pointed distal end 238 and a lumen 240 extending between the ends. Portions of needle cannula 234 between ends 236 and 238 are securely mounted in hub 226. Thus, pointed proximal end 236 of needle cannula 234 projects proximally beyond needle hub 226 to define a non-patient end 242 of needle cannula 234. Similarly, pointed distal end 238 projects distally beyond needle hub 236 to define an IV end 244 of needle cannula 234. A multiple sample sleeve 246 is mounted over the non-patient end 242 of needle cannula 234 and is securely engaged with portions of hub 226 adjacent proximal end 228 thereof.

A tip guard assembly 250 is slidably mounted on IV end 244 of needle cannula 234. Tip guard assembly 250 is substantially identical to tip guard assembly 26 described and illustrated above. More particularly, tip guard assembly 250 includes a housing 252 and a protective clip 254. The construction and function of these components are substantially identical to the corresponding components of the tip guard assembly 26. Accordingly, a further detailed description of those components is omitted herein.

Needle assembly 210 further includes a collapsible guard drive assembly 260. Collapsible guard drive assembly 260 includes a pair of substantially identical leaves 262 that extend from hub 226 to housing 252 of tip guard assembly 250. Each leaf 262 has a width several times greater than the width of needle cannula 234. Leaves 262 are formed from a resilient deformable material, such as silicone, that is capable of collapsing onto itself for defining a plurality of folds. Each leaf 262 includes a proximal end 264 and a distal end 266. Proximal end 264 of each leaf 262 is formed with locking apertures 268 that snap into engagement with locking projections formed on hub 226. Distal ends 266 similarly are formed with locking apertures 270 that snap into engagement with locking projections on housing 252 of tip guard assembly 250. The distance between locking apertures 268 and 270 when leaves 262 are in their extended position is sufficient for permitting tip guard assembly 250 to advance into a position for safely shielding pointed distal end 238 of needle cannula 234.

As shown in FIG. 11, the folded condition of leaves 262 will place a distal fold 272 at a location substantially aligned with distal end 230 of hub 226 and a proximal fold 274 at a location approximately aligned with proximal end 228 of needle hub 226. However, needle assembly 210 is intended for use with needle holder 212. Medical practitioners generally would prefer to perform a fluid collection procedure while gripping the tube holder rather than gripping a more distal position adjacent the needle hub. A simultaneous gripping of tube holder 212 and folded leaves 262 at a location distally of tube holder 212 would require awkward manipulation by a medical practitioner and could lead to an inadvertent passive actuation of shielding before use of needle assembly 210. Accordingly, leaves 262 are formed with gripping tabs 272 that extend proximally from each leaf 262 at a location substantially at proximal fold 274. Gripping tabs 276 extend a sufficient distance to overlie tube holder 212 when needle assembly 210 is mounted to holder 212. Additionally, gripping tabs 276 are formed with gripping bumps 278 or other surface irregularities on an outwardly facing surface thereof to facilitate digital gripping between a thumb and forefinger.

Needle assembly 210 further includes an IV packaging cover 280 that is similar to packaging cover 18 described with respect to the first embodiment. In particular, IV packaging cover 280 performs a dual function of preventing an inadvertent stick with pointed distal end 238 of needle cannula 234 prior to use of needle assembly 210. Additionally, IV packaging cover 280 holds leaves 262 in their collapsed condition for maintaining tip guard assembly 250 in its proximal position. IV packaging cover 280 differs slightly from packaging cover 18 in that open proximal end 282 of IV packaging cover 280 is formed with opposed cut-outs 284 for accommodating folded leaves 262. Needle assembly 210 further may include a non-patient packaging cover (not shown) frictionally mounted over proximal portions of needle hub 226 and protectively covering non-patient end 342 of needle cannula 234 prior to use.

Needle assembly 210 is used with tube holder 212 substantially as shown in FIGS. 9–17. In particular, the non-patient packaging cover (not shown) is removed from needle assembly 210 to expose multiple sample sleeve 246. Multiple sample sleeve 246 and non-patient end 242 of needle cannula 234 then are inserted through mounting aperture 224 at distal end of holder 212. Threads near proximal end 228 of hub 226 are engaged with threads in mounting aperture 224 of holder 212. In this mounted condition, as shown most clearly in FIG. 1, gripping tabs 276 of leaves 262 will lie adjacent outer surface regions of tubular sidewall 218 of holder 212 at positions near distal end 216 of holder 212. The medical practitioner grips tabs 276 between a thumb and forefinger. Secure gripping is facilitated by bumps 278 formed on outer surface regions of tabs 276. Thus, the medical practitioner can simultaneously grip tube holder 212 securely and hold leaves 262 in their collapsed condition. IV packaging cover 280 then is pulled distally and separated from needle assembly 210. As a result, pointed distal end 238 of needle cannula 234 is exposed to permit use of needle assembly 210 and needle holder 212. More particularly, tip guard assembly 250 is maintained in its proximal position on needle cannula 234 by the gripping forces on tabs 276.

The medical practitioner then guides pointed distal end 238 of needle cannula 234 into a targeted blood vessel and shifts the grip to release tabs 276 and to retain a more proximal position on needle holder 212. As a result, leaves 262 resiliently and automatically return toward the unfolded condition, and tip guard assembly 250 slides distally along needle cannula 234. The distal movement of tip guard assembly 250 will stop when the distal end of housing 252 contacts the skin of the patient.

The medical practitioner then inserts one or more evacuated tubes into open proximal end 214 of needle holder 212. The stopper across the evacuated tube is pierced by pointed proximal end 236 on non-patient end 242 of needle cannula 234. Successive samples may be obtained in a conventional manner. Upon collection of a suitable number of samples, the practitioner merely pulls needle holder 12 proximally and away from the patient. As a result, leaves 262 continue to unfold and tip guard assembly 250 automatically slides distally along needle cannula and into a shielding position around pointed distal end 238 of needle cannula 234, as shown in FIGS. 16 and 17. In this position, clip 254 springs over pointed distal end 238 to prevent a re-exposure of pointed distal end 38 of needle cannula 234. Additionally, leaves 262 will prevent further distal movement of tip guard assembly 250 beyond needle cannula 234. Furthermore, leaves 262 are sufficiently wide to prevent inadvertent contact with any part of IV end 244 of needle cannula 34. The safely shielded needle assembly 210 then can be discarded in a sharps receptacle.

Figure 18:
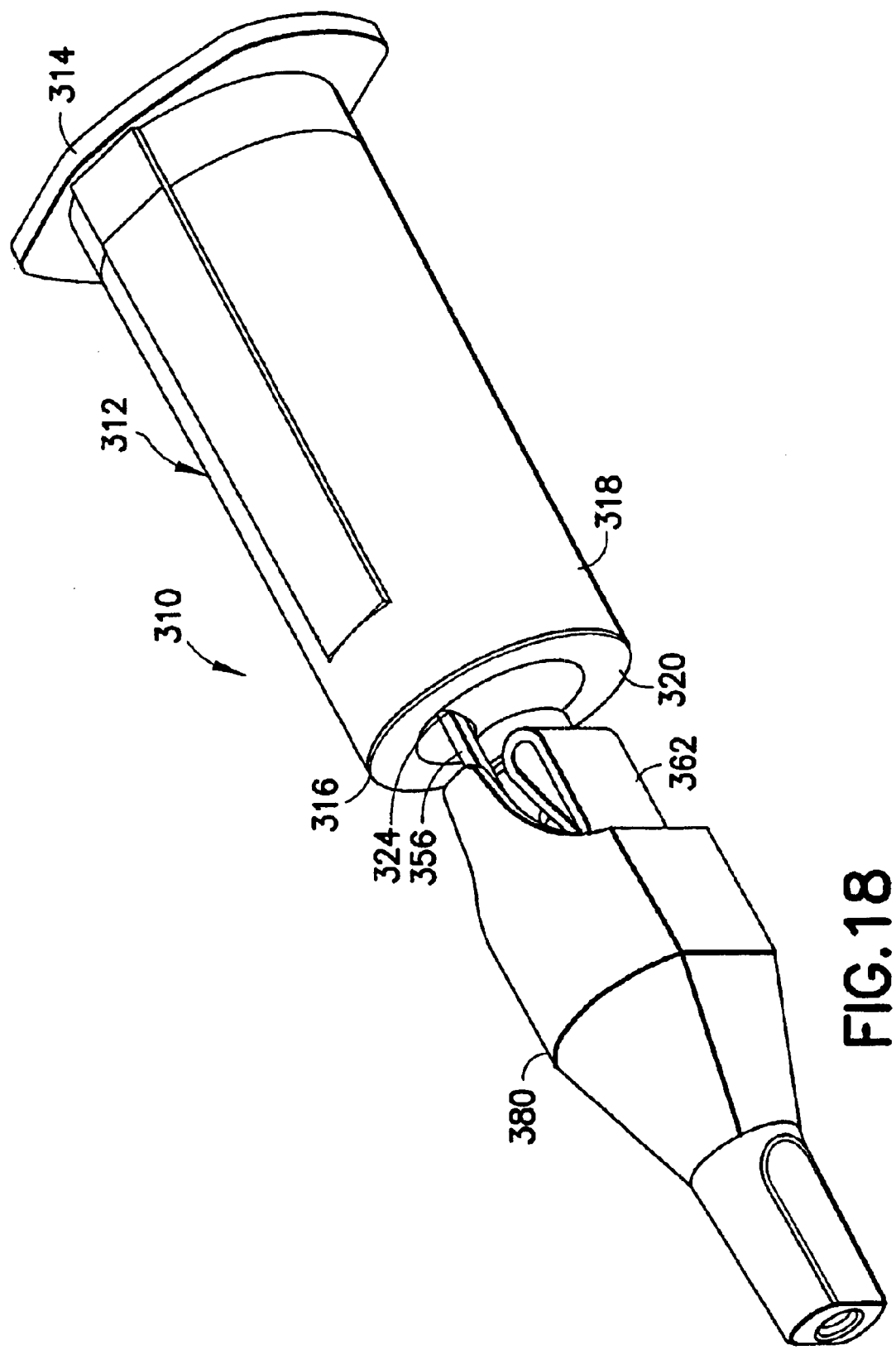
FIG. 18 is a perspective view of a needle assembly and tube holder in accordance with a fourth embodiment of the invention.
Figure 19:
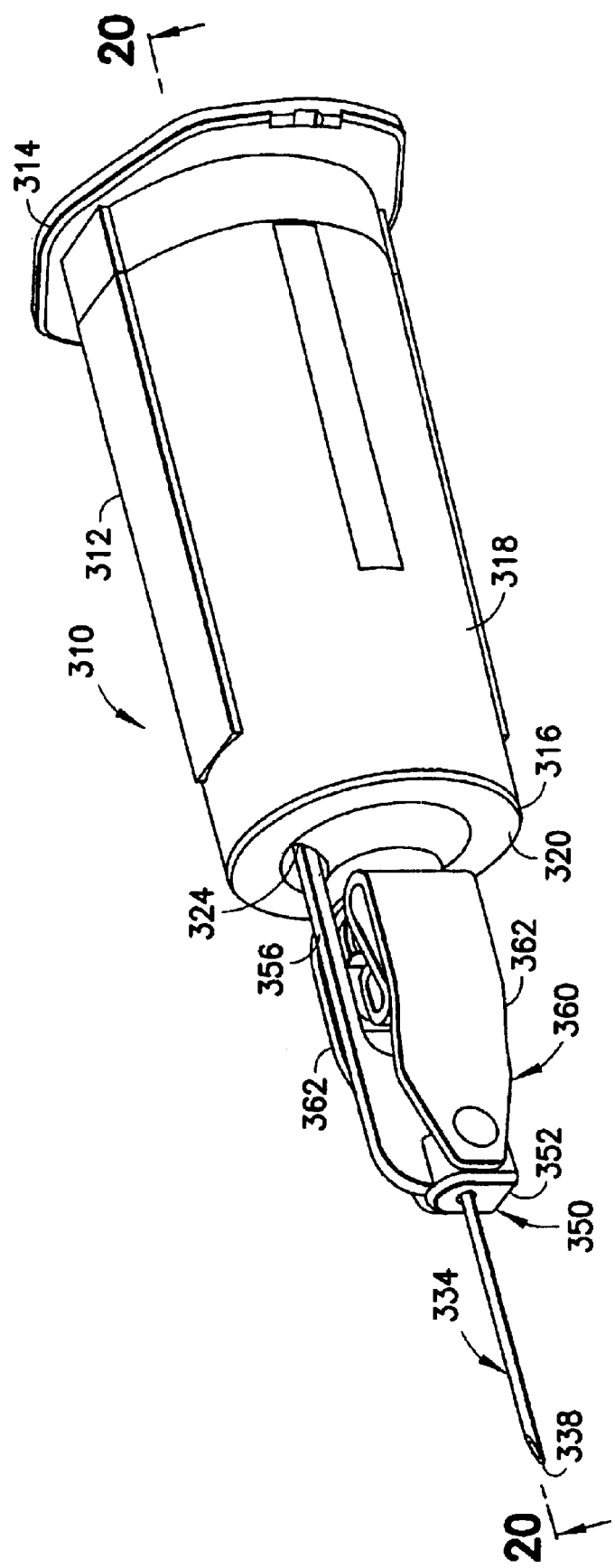
FIG. 19 is a cross-sectional view similar to FIG. 18, but showing the packaging shield removed.
Figure 20:
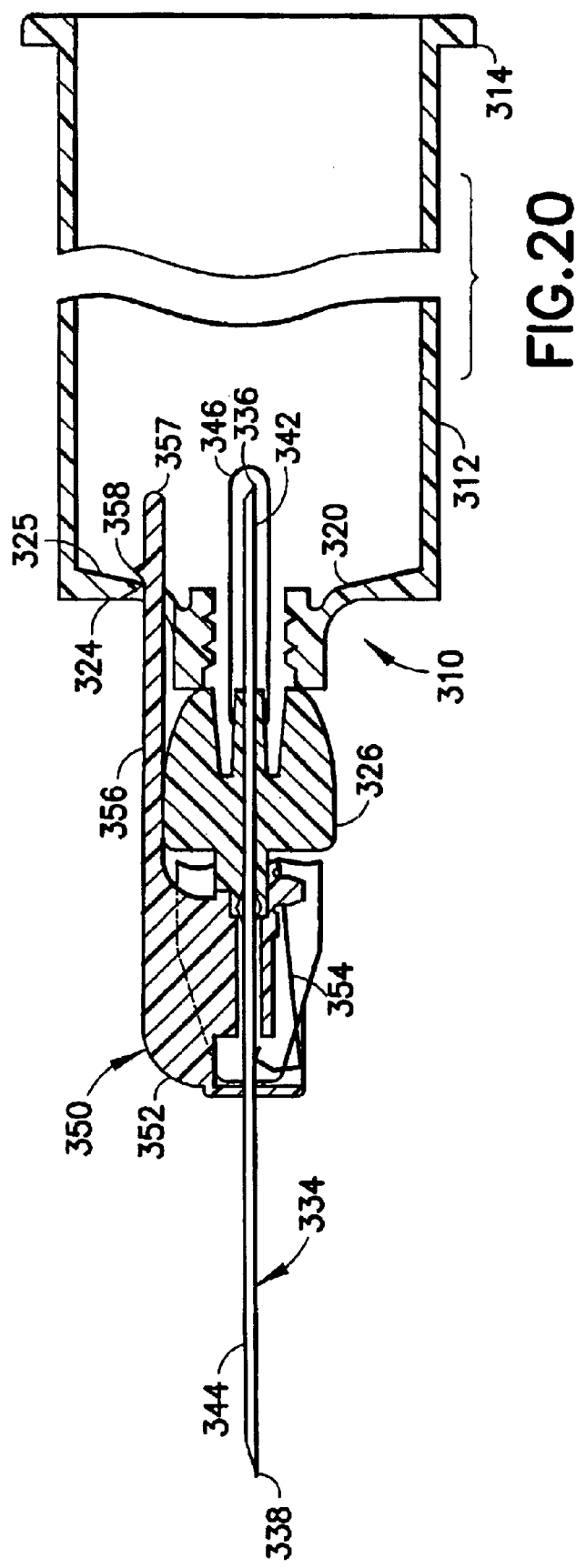
FIG. 20 is a cross-sectional view taken along line 20—20 in FIG. 19.
Figure 21:
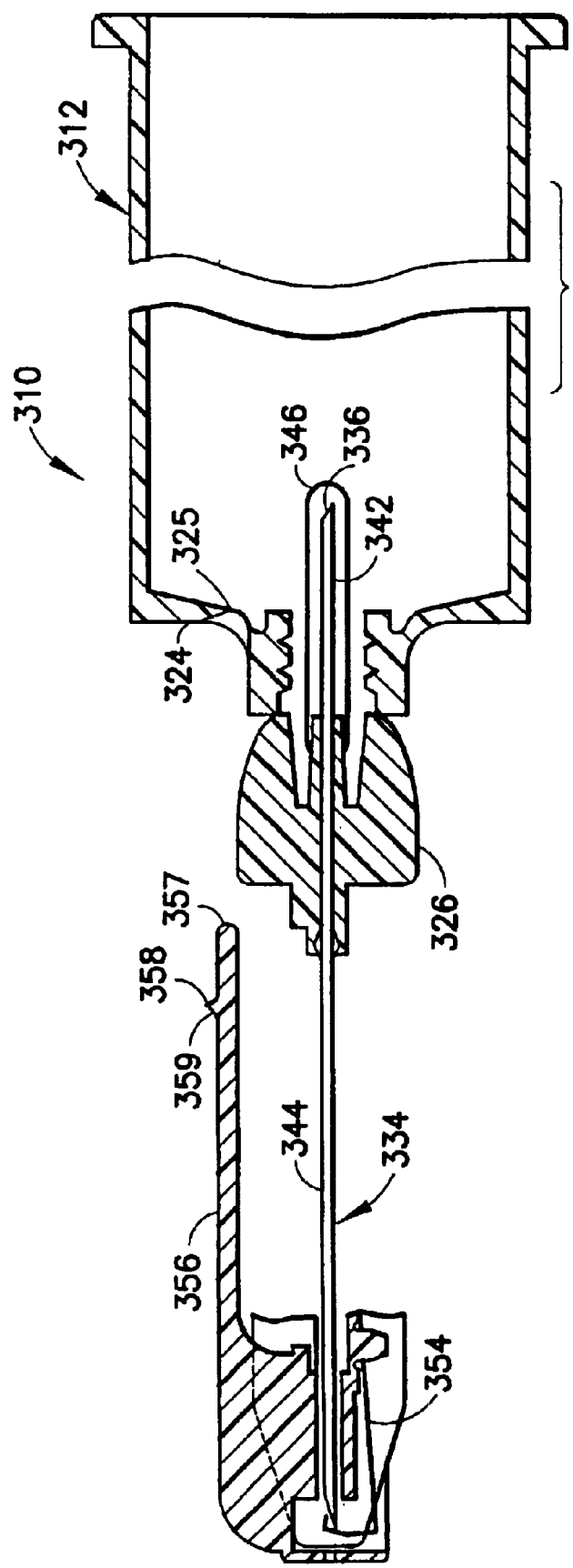
FIG. 21 is a cross-sectional view similar to FIG. 20, but showing the fully shielded condition.

FIGS. 18–21 show a blood collection assembly 310 according to a fourth embodiment of the invention and including an integrated tube holder 312. Holder 312 has a proximal end 314, a distal end 316 and a tubular sidewall 318 extending between the ends. Proximal end 314 is widely open, as shown in FIG. 19, and is configured for slidably receiving an evacuated tube, such as the VACUTAINER® brand of evacuated tubes sold by Becton, Dickinson and Company. Distal end 316 of holder 312 includes an end wall 320 that extends in from tubular sidewall 318. End wall 320 has a mounting aperture 322 to which a needle cannula 310 is mounted. End wall 320 of holder 312 further includes an actuator opening 324 extending entirely therethrough at a location radially outwardly from mounting aperture 322. Actuator opening 324 communicates with interior portions of holder 312, and includes a peripheral locking edge 325.

Assembly 310 includes a needle hub 326 secured adjacent mounting aperture 322 on end wall 320 of holder 312 and a needle cannula 334 secured to needle hub 326. Needle cannula 334 includes a proximal end 336 that projects proximally beyond hub 326 and a distal end 338 that projects distally beyond needle hub 326. Portions of needle cannula 334 between proximal end 336 and hub 326 define a non-patient section 342, whereas portions between distal end 338 and hub 326 define an IV section 344. A multiple sample sleeve 346 is mounted over non-patient section 342 of needle cannula 334. A tip guard assembly 350 is slidably mounted on IV section 344 of needle cannula 334. Tip guard assembly 350 includes a housing 352 and a protective clip 354. Housing 352 is similar to housing 252 of tip guard assembly 250 described and illustrated above. However, housing 352 is formed unitarily with an actuator arm 356 that projects proximally through actuator opening 325 in end wall 320 of holder 312 when housing 352 is in its proximal position on needle cannula 334. Actuator arm 356 has a proximal end 357 and a locking detent 358 near proximal end 357. Locking detent 358 has a sloped distal surface 359.

Assembly 310 further includes a collapsible guard drive assembly 360 that is very similar to the guard drive assemblies of the previous embodiments. More particularly, guard drive assembly 360 includes two substantially identical leaves 362 that extend from hub 326 to housing 352 of tip guard assembly 350. Leaves 362 are formed from a resilient deformable material, such as silicone, that are capable of collapsing into folded conditions, as shown in FIGS. 18 and 19. Each leaf 362 has a proximal end 364 and a distal end 366 that are secured respectively to hub 326 and housing 352 substantially as described with respect to comparable parts of the previous embodiment. Additionally, as in the previous embodiment, leaves 362 are dimensioned for permitting tip guard assembly 350 to advance into a position for safely shielding pointed distal end 338 of needle cannula 334. Leaves 362 need not have gripping tabs comparable to gripping tabs 276 of the preceding embodiment. In this regard, the gripping tabs of the preceding embodiment had been provided to hold the tip guard in its proximal position. However, locking detent 358 near proximal end 357 of actuating arm 354 releasably holds tip guard 352 in its proximal position, and hence avoids the need for gripping tabs.

Needle assembly 310 is sold as an integrated unit that includes holder 312, hub 326, needle cannula 334, tip guard assembly 350, guard drive assembly 360 and a packaging shield 380. This assembly is employed by removing the device from its blister package or other such packaging. The packaging shield 380 then is removed to expose pointed distal end 338 of needle cannula 334. Actuator arm 354 extends through actuator opening 324, and locking detent 358 engages locking edge 325 on distal end wall 320. Thus, the device is stable in this condition. Additionally, it is unnecessary for the user to grip portions of the leaves for holding the leaves in a collapsed condition. The user then performs the specified preparation work and accesses the blood vessel with the distal end 338 of needle cannula 334. An evacuated tube then is inserted into open distal end 314 of holder 312. Sufficient insertion of the evacuated tube into holder 312 causes the tube to engage proximal end 357 of actuator arm 354. As a result, sloped distal surface 359 of locking detent 358 will slide against locking edge 325, and actuator arm 354 will be deflected sufficiently for locking detent 358 to pass through actuating aperture 325. As a result, leaves 362 will expand resiliently and propel tip guard assembly 350 into contact with the skin of the patient. One or more samples of blood can be drawn in the conventional manner. After the last sample of blood has been drawn, holder 312 is pulled away from the patient. Leaves 362 will cause tip guard assembly 350 to be propelled the remainder of its distance into surrounding relationship with the pointed distal end 338 of needle cannula 334. As in the previous embodiments, protective clip 354 in housing 352 of tip guard assembly 350 will prevent tip guard assembly 350 from moving proximally from the shielded position. Similarly, leaves 362 prevent tip guard assembly 350 from moving distally beyond the needle cannula 334.

The invention has been described and illustrated with respect to certain preferred embodiments. However, other embodiments are within the scope of the invention as defined by the appended claims. For example, the illustrated embodiment shows a tip guard assembly 350 with an actuator arm 356 that extends integrally from housing 352. The actuator arm 356 engages an opening 325 in end wall 320 of holder 312. This illustrated embodiment offers several efficiencies with respect to molding, inventory management and assembly. However, a plurality of parts can achieve the above-described functions and may be preferable in certain situations. Thus, an actuator comparable to the actuator arm 356 may be slidably mountable to holder 312 and may be formed separately from a housing that holds protective clip 354. The actuator may be releaseably engaged with structure on or near the housing that holds protective clip 354. Insertion of a tube into holder 312 will generate sufficient movement of the actuator to initiate the movement of the tip guard assembly in a distal direction along needle cannula 334. The above-described collapsible guard drive assembly then will be free to propel the tip guard assembly the remainder of the distance in the distal direction and into shielding disposition around the tip of needle cannula 334. These and other variations will be apparent to a person skilled in this art after having read the subject disclosure and are encompassed by the claims of the subject invention.

What is claimed is:

1. A passively shieldable needle device comprising:

a tube holder having a proximal end, a distal end and a tube receptacle between said ends, a distal end wall at the distal end of the tube holder, the distal end wall having an actuator aperture extending therethrough and into communication with said tube receptacle;

a needle cannula mounted to said distal end of said tube holder and having a distal end projecting distally beyond said tube holder;

a tip guard movable along said needle cannula from a proximal position substantially adjacent said tube holder to a distal position where said tip guard protectively shields said distal end of said needle cannula;

a collapsible guard drive including a pair of resiliently deformable leaves for propelling said tip guard into said distal position; and an actuator passing through the actuator aperture and having a proximal end in said tube receptacle and a distal end projecting distally from said tube holder and configured for exerting a pushing force on said tip guard in response to insertion of said tube into said tube receptacle, said actuator having a locking detent releasably engaged with said tube holder for releasably holding said tip guard in said proximal position, said actuator being configured for engagement by a tube inserted into said tube receptacle of said tube holder and being movable distally for initiating distal movement of said tip guard from said proximal position.

2. A passively shieldable needle device comprising:

a tube holder having a proximal end, a distal end and a tube receptacle between said ends, a needle cannula mounted to said distal end of said tube holder and having a distal end projecting distally beyond said tube holder;

a tip guard movable along said needle cannula from a proximal position substantially adjacent said tube holder to a distal position where said tip guard protectively shields said distal end of said needle cannula;

a collapsible guard drive for propelling said tip guard into said distal position, said collapsible guard drive including a pair of resilient deformable leaves, each said leaf having a proximal end fixed in proximity to said distal end of said tube holder and a distal end connected to said tip guard, said leaves being foldable and collapsible substantially adjacent to said tube holder when said tip guard is in said proximal position, said leaves further being resiliently movable toward a non-collapsed condition for propelling said tip guard to said distal position on said needle cannula; and an actuator having a proximal end in said tube receptacle and a distal end, said actuator being configured for engagement by a tube inserted into said tube receptacle of said tube holder and being movable distally for initiating distal movement of said tip guard from said proximal position.

3. The needle device of claim 2, wherein said actuator includes a locking detent for releasably holding said tip guard in said proximal position prior to insertion of said tube into said tube receptacle.

4. The needle device of claim 3, wherein said tube holder includes a distal end wall with an actuator aperture extending therethrough and into communication with said tube receptacle, said actuator extending through said actuator aperture and having a distal end projecting distally from said tube holder.

5. The needle device of claim 4, wherein the distal end of the actuator is configured for exerting a pushing force on said tip guard in response to insertion of said tube into said tube receptacle.

6. The needle device of claim 5, wherein the actuator is formed unitarily with said tip guard.

7. The needle device of claim 5, wherein said actuator includes a locking detent releasably engaged with said tube holder.

8. The needle device of claim 2, wherein said leaves are formed from silicone.

9. The needle device of claim 2, wherein said leaves are disposed on opposite sides of said needle cannula, said leaves further having a width for substantially preventing contact with portions of said needle cannula between said hub and said tip guard when said leaves have propelled said tip guard into said distal position on said needle cannula.

10. A passively shieldable needle device comprising:

a tube holder having a proximal end, a distal end and a tube receptacle between said ends, said distal end of said tube holder including a distal end wall with an actuator aperture extending therethrough and into communication with said tube receptacle;

a needle cannula mounted to said distal end of said tube holder and having a distal end projecting distally beyond said tube holder;

a tip guard movable along said needle cannula from a proximal position substantially adjacent said tube holder to a distal position where said tip guard protectively shields said distal end of said needle cannula, said tip guard including an actuator arm slidably disposed in said actuator aperture and extending into said tube receptacle when said tip guard is in said proximal position, said actuator arm including a locking detent releasably engaged with a locking structure of said tube holder when said tip guard is in said proximal position; and a collapsible guard drive for propelling said tip guard into said distal position, whereby movement of said tip guard distally from said proximal position is initiated by engagement of said actuator arm by a tube inserted into said tube receptacle of said tube holder.

11. The needle device of claim 10, wherein the locking structure is a locking edge formed on a portion of said distal end wall of said tube holder substantially adjacent said actuator aperture.

12. A passively shieldable needle device comprising:

a tube holder having a proximal end, a distal end and a tube receptacle between said ends, said distal end of said tube holder including a distal end wall with an actuator aperture extending therethrough and into communication with said tube receptacle;

a needle cannula mounted to said distal end of said tube holder and having a distal end projecting distally beyond said tube holder;

a tip guard movable along said needle cannula from a proximal position substantially adjacent said tube holder to a distal position where said tip guard protectively shields said distal end of said needle cannula, said tip guard including an actuator arm extending through said actuator aperture and into said tube receptacle when said tip guard is in said proximal position; and a collapsible guard drive for propelling said tip guard into said distal position, whereby movement of said tip guard distally from said proximal position is initiated by engagement of said actuator arm by a tube inserted into said tube receptacle of said tube holder, said collapsible guard drive including leaves disposed on opposite sides of said needle cannula, said leaves having widths for substantially preventing contact with portions of said needle cannula between said holder and said tip guard when said leaves have propelled said tip guard into said distal position on said needle cannula.

13. A passively shieldable needle device comprising:

a tube holder having a proximal end, a distal end and a tube receptacle between said ends, said distal end of said tube holder including a distal end wall with an actuator aperture extending therethrough and into communication with said tube receptacle;

a needle cannula mounted to said distal end of said tube holder and having a distal end projecting distally beyond said tube holder;

a tip guard movable along said needle cannula from a proximal position substantially adjacent said tube holder to a distal position where said tip guard protectively shields said distal end of said needle cannula, said tip guard including an actuator arm extending through said actuator aperture and into said tube receptacle when said tip guard is in said proximal position; and a collapsible guard drive for propelling said tip guard into said distal position, whereby movement of said tip guard distally from said proximal position is initiated by engagement of said actuator arm by a tube inserted into said tube receptacle of said tube holder said collapsible guard drive including a pair of resilient deformable leaves, each said leaf having a proximal end fixed in proximity to said distal end of said tube holder and a distal end connected to said tip guard, said leaves being foldable and collapsible substantially adjacent to said tube holder when said tube holder is in said proximal position, said leaves further being resiliently movable toward a non-collapsed condition for propelling said tip guard to said distal position on said needle cannula.

14. The needle device of claim 13, wherein said leaves are formed from silicone.

15. The needle device of claim 13, wherein said leaves are disposed on opposite sides of said needle cannula, said leaves further having a width for substantially preventing contact with portions of said needle cannula between said hub and said tip guard when said leaves have propelled said tip guard into said distal position on said needle cannula.

16. A passively shieldable needle device comprising:
a tube holder having a proximal end, a distal end and a tubular sidewall extending between said ends, said proximal end of said tube holder being open to define a tube receptacle, said distal end of said tube holder including a distal end wall with a cannula aperture and an actuator aperture extending therethrough and into communication with said tube receptacle;
a needle cannula mounted to said cannula aperture of said tube holder and having a distal end projecting distally beyond said tube holder;
a tip guard slidably movable along said needle cannula from a proximal position substantially adjacent said tube holder to a distal position where said tip guard protectively shields said distal end of said needle cannula, said tip guard including an elongated actuator arm extending substantially parallel to said needle cannula through said actuator aperture and into said tube receptacle when said tip guard is in said proximal position, said actuator arm having a locking detent formed thereon and being resiliently engageable with portions of said tube holder adjacent said actuator aperture; and
a pair of resiliently deformable leaves, each said leaf having a proximal end fixed in proximity to said distal end wall of said tube holder and a distal end connected to said tip guard, said leaves being foldable and collapsible substantially adjacent to said tube holder when said tube holder is in said proximal position, said leaves further being resiliently movable toward a non-collapsed condition for propelling said tip guard to said distal position on said needle cannula.

17. The needle device of claim 16, wherein the actuator arm is configured for sliding movement through said actuator aperture.

* * * * *